United States Patent
Ung-Chhun et al.

(10) Patent No.: US 6,648,922 B2
(45) Date of Patent: Nov. 18, 2003

(54) METHOD FOR PRODUCING IMPROVED MEDICAL DEVICES AND DEVICES SO PRODUCED

(75) Inventors: Neng S. Ung-Chhun, Lincolnshire, IL (US); Richard J. Johnson, Mundeline, IL (US); Dean Laurin, Chandler, AZ (US); Crystal M. Cunanan, Mission Viejo, CA (US)

(73) Assignee: Baxter International Inc., Deerfield, IL (US)

( * ) Notice: Subject to any disclaimer, the term of this patent is extended or adjusted under 35 U.S.C. 154(b) by 165 days.

(21) Appl. No.: 09/790,395

(22) Filed: Feb. 21, 2001

(65) Prior Publication Data

US 2001/0012538 A1 Aug. 9, 2001

Related U.S. Application Data

(62) Division of application No. 09/388,913, filed on Sep. 1, 1999, now Pat. No. 6,306,454, which is a continuation-in-part of application No. 09/211,620, filed on Dec. 15, 1998, now abandoned, which is a continuation-in-part of application No. 08/971,887, filed on Nov. 11, 1997, now Pat. No. 5,972,217, which is a continuation-in-part of application No. 08/810,751, filed on Mar. 4, 1997, now Pat. No. 5,795,483, which is a division of application No. 08/323,559, filed on Oct. 17, 1994, now Pat. No. 5,647,985.

(51) Int. Cl.⁷ ................................................. A61F 2/36
(52) U.S. Cl. .................................. 623/23.72; 623/23.76
(58) Field of Search .............................. 623/1.41–1.48, 623/2.42, 15.11, 15.12, 23.72, 23.73–23.76

(56) References Cited

U.S. PATENT DOCUMENTS

| | | |
|---|---|---|
| 3,945,926 A | 3/1976 | Kesting |
| 4,053,420 A | 10/1977 | Marx |
| 4,130,642 A | 12/1978 | Kikygawa et al. |
| 4,256,588 A | 3/1981 | Hoehn et al. |
| 4,283,289 A | 8/1981 | Meyst et al. |
| 4,301,144 A * | 11/1981 | Iwashita et al. ................ 514/6 |
| 4,330,410 A | 5/1982 | Takenaka et al. |

(List continued on next page.)

FOREIGN PATENT DOCUMENTS

| | | |
|---|---|---|
| AU | 58983/90 | 1/1991 |
| EP | 0 370 584 | 5/1990 |
| EP | 0 397 403 | 11/1990 |
| EP | 0 406 485 | 1/1991 |
| EP | 0 408 462 | 1/1991 |

(List continued on next page.)

OTHER PUBLICATIONS

Grimm et al., "Glutaraldehyde Affects Biocompatibility of Bioprosthetic Heart Valves," Surgery, 1992, vol. 111, No. 1:74–78.

Golomb et al., "The Role of Glutaraldehyde–induced Cross–links in Calcification of Bovine Pericardium Used in Cardiac Valve Bioprostehses," Amer. J. Pathol., 1987, vol. 127, No. 1:122–130.

Levy et al., "Cardiovascular Implant Calcification: A Survey and Update," Biomaterials, 1991, vol. 12: 707–714.

Harasym et al., "Poly(ethylene glycol)–Modified Phospholipids Prevent Aggregation during Covalent Conjugation of Proteins to Lipsomes," Bioconjugate Chem., 1995, vol. 6, No. 2: 187–194.

(List continued on next page.)

Primary Examiner—David H. Willse
Assistant Examiner—Hieu Phan
(74) Attorney, Agent, or Firm—Joseph Barrett; Bell Boyd & Lloyd LLC

(57) ABSTRACT

Medical devices and methods of producing same are provided. The medical device comprising a body member and a coating on at least a portion of the body member comprising an insitu condensation product of a first electrophilically active, high molecular weight polyalkylene oxide and a second high molecular weight polyoxyalkylene derivative.

17 Claims, 14 Drawing Sheets

U.S. PATENT DOCUMENTS

| | | | |
|---|---|---|---|
| 4,358,476 A | 11/1982 | Zimmer et al. | |
| 4,399,035 A | 8/1983 | Nohmi et al. | |
| 4,416,777 A | 11/1983 | Kuroda et al. | |
| 4,596,657 A | 6/1986 | Wisdom | |
| 4,618,533 A | 10/1986 | Steuck | |
| 4,675,361 A | 6/1987 | Ward, Jr. | |
| 4,701,267 A | 10/1987 | Watanabe et al. | |
| 4,767,541 A | 8/1988 | Wisdom | |
| 4,810,378 A | 3/1989 | Carmen et al. | |
| 4,840,851 A | 6/1989 | Golander et al. | |
| 4,855,063 A | 8/1989 | Carmen et al. | |
| 4,880,548 A | 11/1989 | Pall et al. | |
| 4,915,848 A | 4/1990 | Carmen et al. | |
| 4,917,799 A | 4/1990 | Masuda et al. | |
| 4,919,823 A | 4/1990 | Wisdom | |
| 4,925,572 A | 5/1990 | Pall | |
| 4,936,993 A | 6/1990 | Nomura | |
| 4,936,998 A | 6/1990 | Nishimura et al. | |
| 4,943,287 A | 7/1990 | Carmen | |
| 4,976,861 A | 12/1990 | Pall | |
| 4,985,153 A | 1/1991 | Kuroda et al. | |
| 4,997,577 A | 3/1991 | Stewart | |
| 5,034,135 A | 7/1991 | Fischel | |
| 5,089,146 A | 2/1992 | Carmen et al. | |
| 5,092,996 A | 3/1992 | Spielberg | |
| 5,100,551 A | 3/1992 | Pall et al. | |
| 5,100,564 A | 3/1992 | Pall et al. | |
| 5,104,788 A | 4/1992 | Carmen et al. | |
| 5,128,048 A | 7/1992 | Stewart et al. | |
| 5,190,657 A | 3/1993 | Heagle et al. | |
| 5,194,145 A | 3/1993 | Schoendorfer | |
| 5,229,012 A | 7/1993 | Pall et al. | |
| 5,252,222 A | 10/1993 | Matkovish et al. | |
| 5,258,126 A | 11/1993 | Pall et al. | |
| 5,258,127 A | 11/1993 | Gsell et al. | |
| 5,647,985 A | 7/1997 | Ung-Chhun et al. | |
| 5,795,483 A | 8/1998 | Ung-Chhun et al. | |
| 5,882,850 A * | 3/1999 | Khor et al. | 435/1.1 |

FOREIGN PATENT DOCUMENTS

| | | |
|---|---|---|
| EP | 0 419 346 | 3/1991 |
| EP | 0 500 472 | 9/1993 |
| EP | 0 561 379 | 9/1993 |
| JP | 03000 074 | 12/1988 |
| JP | 05034337 | 7/1991 |
| JP | 05087808 | 9/1991 |
| JP | 05148150 | 11/1991 |
| JP | 05148151 | 11/1991 |
| JP | 4-187206 | 7/1992 |
| JP | 5-194243 | 3/1993 |
| WO | 93/08904 | 5/1993 |
| WO | 93/03740 | 7/1993 |

OTHER PUBLICATIONS

Chen et al., "Effect of 2–amino Oleic Acid Exposure Conditions on the Inhibition of Calcification of Glutaraldehyde Cross–Linked Porcine Aortic Valves," J. Biomed. Mater. Res., 1994, vol. 28: 1485–1495.

O'Brien et al., "The Metronic INtact Xenograft: An Analysis of 342 Patients over a Seven–Year Follow–Up Period," Ann. Thorac. Surg., 1995, vol. 60 (Suppl.): S253–S257.

Breillatt et al., "Recombinant Hirudin Analog Designed for Attachment to Polymers," Abstract FASEB J., 1992, vol. 6, A–1320.

GEndler et al., "Toxic Reactions Evoked by Glutaraldehyde– fixed Pericardium and CardiacValve Tissue Bioprosthesis," Journal of Biomedical Materials Rsearch, 1984, vol. 18: 727–736.

Park et al., "Chemical Modification of Implantable Biologic Tissue for Anti–Calcification," ASAIO Journal, 1993, vol. 40: M377–M382.

Han et al., "In Vivo Biostability and Calcification–Resistance of Surface–Modified PU–PEO–SO3," Journal of Biomedical Materials Research, 1993, vol. 27: 1063–1073.

* cited by examiner

| | | | |
|---|---|---|---|
| PEO-PEO-PEO | ABP-ABP-ABP | PEO-PEO-PEO | ABP-ABP-ABP |
| ABP-ABP-ABP | PEO-PEO-PEO | ABP-ABP-ABP | PEO-PEO-PEO |
| PEO-PEO-PEO | ABP-ABP-ABP | PEO-PEO-PEO | PEO-PEO-PEO |
| \|\|\|\|\|\|\|\|\|\|\|\|\|\|\| | \|\|\|\|\|\|\|\|\|\|\|\|\|\|\| | \|\|\|\|\|\|\|\|\|\|\|\|\|\|\| | \|\|\|\|\|\|\|\|\|\|\|\|\|\|\| |
| a | b | c | d |

FIG. 1

With : 100<n>225
PEO: R=H
Imidazole-PEO: R=-CO-N⟨imidazole⟩
Tetraamino PEO: R=-CONH(CH$_2$)$_2$NH$_2$
Tetraacrylate PEO: R=-CH=CH$_2$ 1. CH$_3$O(CH$_2$CH$_2$O)$_n$CH$_2$CH$_2$O-R 2. ROCH$_2$CH$_2$O(CH$_2$CH$_2$O)$_n$CH$_2$CH$_2$O-R PEO: R=H
Imidazole-PEO: R=-CO-N⟨imidazole⟩
With : 250<n>450

3.  
   A-CH$_2$         CH$_2$-A
CH$_3$CH$_2$-C-CH$_2$-O-CH$_2$-C-CH$_2$-CH$_3$
   A-CH$_2$         CH$_2$-A

A= CH$_2$=CH-COO-CH$_2$CH$_2$O(CH$_2$CH2O)$_{77}$

- Uncoated
- 2.5x T-NH2-PEO
- Imz-PEO

□ Uncoated
× 2.5x T-NH2-PEO
□ Imz-PEO

METHOD FOR PRODUCING IMPROVED MEDICAL DEVICES AND DEVICES SO PRODUCED

This application is a divisional of U.S. patent application Ser. No. 09/388,913 filed on Sep. 1, 1999 now U.S. Pat. No. 6,306,454 which is a continuation-in-part of U.S. patent application Ser. No. 09/211,620, filed on Dec. 15, 1998, now abandoned which is a continuation-in-part of U.S. patent application Ser. No. 08/971,887, filed on Nov. 11, 1997, now U.S. Pat. No. 5,972,217 which is a continuation-in-part of U.S. patent application Ser. No. 08/810,751, filed on Mar. 4, 1997, now U.S. Pat. No. 5,795,483 which is a divisional of U.S. patent application Ser. No. 08/323,559, filed on Oct. 17, 1994 now U.S. Pat. No. 5,647,985.

BACKGROUND OF THE INVENTION

The present invention relates generally to medical devices and products. More specifically the present invention relates to medical devices and products that are coated with a material to provide improved characteristics.

There are literally thousands of products that are used in the medical industry for a variety of treatments and therapies. The surface characteristics of some of these products may be critical to the ability of the products to function. Such products run the gamut from membranes used in blood and cell separation devices, theracyte devices, dialyzers, arterial filters, catheters, wound drains, vascular grafts, and heart valve tissues.

For example, a slippery or low friction surface property is required in various medical devices. These devices include wound drains, chest tubes, guide wires, catheters, and angioplasty products. A lubricious surface is desirable as it reduces pain to the patient during insertion and/or removal of the device.

It is also desirable, on a number of medical products, to provide a surface that has anti-microbial properties. Likewise, medical devices that have surfaces that are non-thrombogenic are valuable in many applications.

In certain applications, it is also desirable to provide a surface that binds to certain type of cells or agents. For example, such products may be desirable for implantable biological tissue such as bioprosthetic valves.

By way of further and more detailed example, in processing whole blood for therapeutic administration to patients, it is desirable to separate the various cellular components. In particular, it is desirable to remove leukocytes because of their role in mediating immunologic reactions which can cause adverse clinical events such as allosensitization. For a review of adverse clinical sequellae to transfusion, see Sekiguchi, et al., *Leucocyte-depleted blood products and their clinical usefulness*, Ch. 5, pg. 26–33, from *The Role of Leucocyte Depletion in Blood Transfusion Practice* (1988). Furthermore, leukocytes are unessential for therapeutic supplementation of cell deficiencies in patients involving platelets and red cells. Thus, filter systems have been devised for passaging blood cells in order to remove leukocytes while allowing platelets or red blood to pass through for subsequent recovery.

There have been a number of approaches reported for leukocyte depletion. U.S. Pat. No. 4,330,410 discloses a packed fiber mass with leukodepletion properties comprising fibers of cellulose acetate, acrylonitrile, polyamide, or polyester. U.S. Pat. No. 4,925,572 discloses the use of a gelatin coating to inhibit red blood cell (RBC) and platelet adhesion. Leukodepletion is accomplished primarily through physical entrainment of the cells in the fiber body, and adhesion of RBCs and platelets results from the gelatin coating. U.S. Pat. No. 4,936,998 discloses a strategy for leukodepletion in which a hydrophilic monomer containing hydroxyl or amido groups and functional nitrogen-containing groups such as primary or secondary amino groups is coated onto a filter matrix of known fibers such as polyester, polyamide, etc.

Modification of fiber surfaces has also been used to obtain materials with improved cell separation properties. For example, U.S. Pat. No. 4,130,642 discloses a packed column in which the packing material comprises an Egyptian cotton which has been de-fatted and bleached so that RBC readily pass through the column.

Some separation strategies involve multiple steps. U.S. Pat. No. 4,925,572 discloses a multistep method comprising an upstream porous element for removal of gels, a second element of finer porosity for removal of aggregated matter, and a final filtration step involving common fibers to which surface tension-reducing and improved wetting are obtained by radiation grafting of biocompatible moieties. Further description of leukodepletion methods is contained in Rikumaru, et al., *Advanced methods for leucocyte removal by blood filtration*, Ch. 6, pgs. 35–40, from *The Role of Leucocyte Depletion in Blood Transfusion Practice* (1988).

It is of utmost importance in designing leukodepletion strategies in which one goal is to obtain good recoveries of platelets and RBCs, to achieve separations without activating platelets or complement. It is also important that any coatings utilized to enhance the separations not be leached into solution, since the recovered cells are intended for intravascular administration to patients. One approach embodies a filter composed of a porous polymer material with continuous pore structure having a coating combining a nitrogen-containing functional group with a polyethylene oxide chain having 2–15 repeating units (See Jap. Kokai Patent Application No. Hei 5 [1993]-194243). This material is said to entrap leukocytes while giving high yields of platelets.

The use of polyalkylene oxide polymers is well-known in the construction of biocompatible materials, because of its low biological activity in activating cellular and humoral components of blood, and in stimulating immune responses. However, the inertness of the polyalkylene oxide polymers may also interfere with the degree of separation that can be obtained with cell separation filters, unless combined with functional groups that enhance separation parameters. A suitable combination of coating components has not heretofore been developed which is efficacious for cell separations from whole blood as distinct from semi-purified cell suspension mixtures.

Likewise, for a number of other medical products, a suitable material or combination for coating products has not been provided.

SUMMARY OF THE INVENTION

The present invention provides improved methods for coating medical products and devices. Additionally, the present invention provides improved coated medical devices and products.

Summarizing briefly, the present invention provides, in an embodiment, medical devices which are coated, at least in part, with a chemical condensation product, prepared by reaction in-situ of a first electrophilically active, high molecular weight polyalkylene oxide, and a second high molecular weight polyalkylene oxide derivative. In an embodiment, the derivative can be either a tetraaminopolyalkylene oxide or a bifunctional dihydroxy- or diaminopolyoxyalkylene derivative, or combination thereof. In another embodiment, the coating may be an isopolymer of a high molecular weight tetraacrylatepolyalkylene oxide, polymerized by exposure to radiation.

The condensation reaction occurs in-situ, e.g. after one polymer is placed onto a surface, the second polymer is then contacted with the surface and specifically the first polymer, and the condensation reaction occurs spontaneously at a temperature between 5 degrees and about 200 degrees centigrade. The electrophilically active, high molecular weight polyalkylene oxide compound has the general structure Y-PEO-R-PEO-Y wherein Y is a reactive moiety selected from an oxycarbonylimidazole, tresyl-, tosyl-, N-hydroxysuccinimidyl, and p-nitrophenyl-activated esters; acrylates; glycidyl ethers; and aldehydes. The oxycarbonylimidazole leaving group is preferred, as will be apparent from the detailed specification, R is a spacer molecule (a chemical backbone) consisting of either bisphenol A (4,4'-(1-methylethylidene)bisphenol) or bisphenol B (4,4'-(1-methylpropylidene)bisphenol), and PEO stands for polyalkylene oxide.

In a method of preparing the material of the present invention, a first polymer comprising an electrophilically active, high molecular weight polyalkylene oxide compound, having terminal leaving groups as indicated herein above, oxycarbonylimidazole being preferred, is applied to the surface, then drying the first polymer onto the surface, followed by applying a second polymer consisting of either a tetraamino-, a diamino-, or a dihydroxy- polyalkylene oxide, or combination thereof. The reaction between the polymers occurs spontaneously, and an incubation at a temperature from about 5 degrees to about 200 degrees Centigrade is continued for a time sufficient to obtain substantial completion of crosslinking.

To this end, in an embodiment, the present invention provides a medical device comprising a body member and a coating on at least a portion of the body member comprising an in-situ condensation product of a first electrophilically active, high molecular weight polyalkylene oxide and a second high molecular weight polyoxyalkylene derivative.

In an embodiment, the portion of the body member is constructed at least in part from polyvinyl chloride.

In an embodiment, the portion of the body is constructed at least in part from silicone.

In an embodiment, the portion of the body is biological tissue.

In an embodiment, the coating provides a lubricious surface.

In an embodiment, the coating includes a third component.

In an embodiment, the coating includes a functional group that modifies the surface.

In an embodiment, the functional group is chosen from the group consisting of anti-coagulants, heparin, hirudin, anti-microbial, proteins, peptides, and biopolymers.

In an embodiment, the coating provides a multilayer structure.

In an embodiment, the coating provides an anti-thrombogenic surface.

In an embodiment, the coating provides a noninflammatory surface.

In an embodiment, the coating provides an anti-bacterial surface.

In another embodiment, the present invention provides a medical device designed to be at least partially inserted into a patient comprising a body member that includes on a portion thereof a coating of a polyalkylene oxide that is cross-linked with a polyalkylene oxide derivative to form a coating that provides a lubricous surface.

In an embodiment, the coating includes water.

In an embodiment, the coating includes a functional group that provides a modified surface property to the coating.

In an embodiment, the device is a catheter.

In an embodiment, the device is a wound drain.

In an embodiment, the device is a guide wire.

In an embodiment, the device is a chest tube.

In an embodiment, the portion thereof is constructed from silicone.

In an embodiment, the portion thereof is constructed from polyvinyl chloride.

In another embodiment, the present invention provides an implantable biological tissue comprising a biological tissue and a coating thereon including a multilayer surface including a high molecular weight polyalkylene oxide derivative and a biopolymer.

In an embodiment, the tissue is a vascular graft.

In an embodiment, the tissue is a heart valve tissue.

In an embodiment, the tissue is a synthetic membrane.

In a still further embodiment, the present invention provides a bioprosthetic device comprising a biological tissue coated at least in part with a coating including a polyalkylene oxide derivative that is cross-linked with a polyalkylene oxide derivative.

Additionally, the present invention provides methods of providing medical devices. In an embodiment, the method comprising the steps of providing a medical device having a body and coating at least a portion of the body with a coating including a polyalkylene oxide derivative cross-linked with polyalkylene oxide derivative to modify the surface properties of the portion of the body.

BRIEF DESCRIPTION OF THE DRAWINGS

FIGS. 1a–1d illustrate alternative modes of preparing multiple layers of PEO and biopolymers onto a surface.

DETAILED DESCRIPTION OF THE PREFERRED EMBODIMENT

Figure 2:
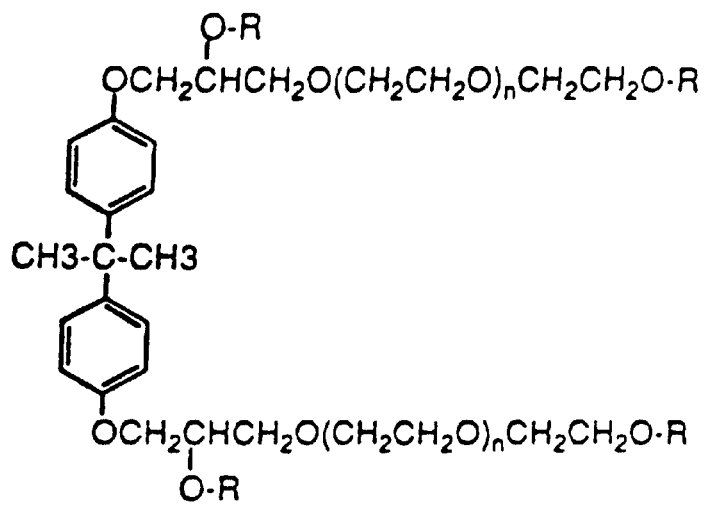
FIG. 2 is a schematic of the chemical structure of the polymers of a preferred embodiment.

The present invention provides medical products having a coating applied thereto which changes the surface properties. Additionally, the present invention provides methods for producing such products.

Pursuant to the present invention products are provided having a surface thereof that includes a PEO cross-linked coated surface. Due to the modified PEO surface certain advantages are provided.

For example, improved bioprosthetic devices can be provided. In this regard, the PEO coating technology can be applied to various types of biological tissues, such as bovine pericardium or porcine aortic tissues, that have been chemically pre-treated with Denacol and/or glutaraldehyde for the development of bioprosthetic heart valves. The method is based on a preliminary coating of tissue in an aqueous solution containing electrophilically active PEO derivatives, preferably a bis-oxycarbonyl-diimidazole-active PEO (Imz-PEO), having an average molecular weight of 20,000 daltons. The resulting intermediate Imz-PEO-activated tissue was further cross-linked with an amino-PEO derivative (preferably of the same MW) to form a stable PEO-coated surface.

This intermediate activated Imz-PEO-coated tissue can also be used to couple proteins, such as avidin into this matrix. This avidin-PEO-coated surface can be further employed to bind biotinylated agents, such as peptides like GREDVY, in order to produce surfaces capable of capturing endothelial cells.

PEO-coated tissues prepared by the above techniques have been shown to reduce fibrinogen binding, compared to uncoated tissue. Other potential advantages of such PEO-modified surfaces include: reduced protein adsorption; limit complement activation; eliminate protein aggregation; produce specific ligand or cell attachment sites through avidin-biotin chemistry; and intermediate activated PEO-coated-tissues can be used for attachment sites to other anti-calcification agents such as 2-amino-oleic acid or toluidine blue.

By way of further example, the surface of certain devices such as wound drains, chest tubes, guide wires, catheter, and angioplasty products can be modified with a PEO coating to make them lubricious. To this end, such lubricious surfaces can be produced using a simple surface modification technology based on a direct coating of high molecular weight polyethylene oxide (PEO) derivatives onto polymeric tubes, using water as a solvent. The polymer materials can be varied from polyvinyl chloride (PVC) to silicone or other type of polymers that are typically used for medical devices. These materials include polyurethane, polyolefine, polyethylene, polypropylene, metal or alloy.

The PEO derivatives are functionalized PEO that could contain an electrophilically active compound such as oxycarbonyl-imidazoyl-PEO (Imz-PEO) or nucleophilically active such as amino-PEO ($NH_2$-PEO). This technology provides a coating that generates low-friction or lubricious surfaces which also can limit fibrinogen adsorption. It has been found that the PEO-coated PVC and PEO-coated silicone tubes are stable in saline or plasma at 37° C. for several days. Also, they can be sterilized with ETO without loss of lubricity or of low protein adsorption properties.

This technology presents several advantages including a simple coating technology that uses water as a solvent. It also allows the production of lubricious surface on PVC and/or silicone surfaces. The production of products having surfaces with low fibrinogen adsorption. It provides the availability of functional groups that allow further surface modification (e.g., coupling with anti-coagulant substances, heparin or hirudin) or anti-microbial ligand (e.g. chitosan). The technology also provides a coating that can be also sterilized with ETO (or gamma) without loss of lubricity or low protein binding ability. The technology also provides the potential application to a variety of other synthetic polymers (polyurethane, polyethylene, polyolefine, and metal or alloy).

Still further pursuant to the present invention multilayer coating can be used to provide new surface modifications. To this end, the present invention provides a new surface modification method that is based on multilayer coatings between high molecular weight PEO derivatives and anti-coagulant biopolymers containing terminal primary amine groups.

The base material can be a wide variety of materials. For example, the base material, could be derived from any biological tissue such as vascular grafts or heart valve tissues, or synthetic membranes made from various hydrophobic or hydrophilic polymers. Biopolymers containing amino-terminal groups can be derived from carbohydrate structures such as heparin (glycosaminoglycan family) and chitosan or proteins such as hirudin.

FIG. 1, and specifically FIGS. 1a–1d, set forth examples of multilayer structures that can be produced. In the figures, the base material has thereon the multilayer coating. PEO refers of course to the polyethylene oxide coating discussed herein. ABP refers to the anticoagulant biopolymers.

These multiple layers of coating may provide numerous advantages. One of the advantages is to provide a permanent coating technique that assures complete coverage of the base material. Additionally, the multiple layers allow the production of a highly anti-thrombogenic surface due to the combined presence of PEO and anticoagulants (heparin or hirudin). Further, the multiple layers allow the production of a non-inflammatory (e.g. non-complement activating) material due to the presence of PEO and heparin. Still further the multilayers allow the production of a potential anti-bacterial surface because of the presence of chitosan. The multilayer coating has applicability to multiple devices, including: membranes; theracyte devices; arterial filter membranes, and oxygenators; catheters, wound drains; and vascular grafts or heart valve tissues.

In another embodiment a blood cell fractionation means is provided comprising a matrix having a fibrous structure and the matrix further characterized in having a coating applied to it which changes its surface properties with respect to cellular adherence of blood cell containing fluid coming into contact therewith. The matrix can be a packing material contained within a column, or a fibrous material compressed into a filter and held in a filter housing of conventional design and construction, although other configurations of a solid matrix contacting a fluid are within the scope of the invention. In an embodiment, the coating of polymers and the chemical reactions which are carried out to create a generally molecularly continuous polymeric surface on the matrix fibers do not require covalent or noncovalent interaction with any chemical moiety present on the native surface of the matrix, the coating itself is independent of the chemical and physical identity of the matrix. Thus, the coating is intended to be universally applicable to any filter available in the cell separation art. Examples include, without limitation, filters having a high glass content, as in glass fiber mats, filters with less or no glass content such as a filter comprising a mixture of glass and polyester, and a polyethylene terephthalate platelet filter coated with hydroxyethylmethyl-methacrylate.

Filter housings which may be conveniently used are manufactured conventionally. Examples of such housing are Swinney plastic manifolds manufactured by Gelman, pediatric Enterprise Housings, or Intermediate Enterprise Housings. The correct size correlations of filters to correspondingly suitable housings will be apparent to those skilled in the art. The only limitation applicable to the blood cell fractionation means is a surface which is incompatible with the polymer solutions. Even in the instance where molecular wetting is not obtainable with the polymer solutions, techniques utilizing emulsifiers and phase penetrants may be useful in achieving adequate coating. To Applicants' knowledge, none of the blood cell fractionation filter materials currently available commercially are to be excluded from applicability to the present invention.

In the method of separating cells using the product of the invention, a cell suspension or whole blood is filtered through the filter having the polymer coating as disclosed. The leukocytes adhere, and the platelets and RBCs pass through the in the filtrate. More generalized methods of contacting the filter with a cell containing fluid are contemplated by this invention as well. For example, contracting by passaging through a packed column, or mixing cells in bulk with dispersed matrix in solution may be employed.

As noted above, the method of the present invention is applicable to a number of products and surfaces. For example, manufacturing ease, chemical condensation reaction of the respective polymers can be carried out insitu, i.e. a first free polymer is laid down on the matrix and dried, and then the second is contacted in solution with the matrix. The ensuing reaction then produces a skin-like sheet or layer of copolymerized material at the surface or the matrix. This reaction in a preferred embodiment proceeds spontaneously at temperatures generally in the range of 5 to 200 degrees centigrade. It is evident that the time for completion of the reaction will be slightly longer at cooler temperatures than for higher temperatures in accordance with kinetic thermodynamic principles. Generally, these reactions may be carried out at ambient temperatures, as disclosed in the Examples, but very little experimentation will be required by those skilled in the art to adjust the reaction times to a particular desired temperatures of reaction.

The first polymer to be contacted with the surface is a high molecular weight electrophilically active polyalkylene oxide. Electrophilically active means that a polyalkylene oxide polymer contains a oxycarbonyl moiety reactive with a nucleophilic center such as an amino or hydroxyl group contained in a second polymer. In a preferred embodiment, a primary amine serving as a nucleophile, reacts with the carbonyl group of the imidazole-polyalkylene oxide polymer to form, upon reaction, an N-substituted carbamate bond where the carbonyl moiety from a cross-linker is incorporated into the new bond. These polymer entities must be high molecular weight, in the range of about 13,000 to 24,000 daltons, preferably about 20,000 daltons. Thus preferred molecules shown in FIG. 2 for reaction on surfaces will have n values of about 100–225.

A first electrophilic polyalkylene oxide polymer will have a terminal leaving group reactive with an amine or hydroxyl containing second polyalkylene oxide. Suitable leaving groups on the first polymer for achieving acceptable chemical condensation are imidazoyl-, tresyl-, tosyl-, acryloyl-, and N-hydroxysuccinimidyl-. Additionally the structure of the electrophilic polymer can further be defined by the general expression: Y-PEO-R-PEO-Y, wherein Y is selected from the following group singly or in combination: oxycarbonylimidazole; tresyl-, tosyl-, N-hydroxysuccinimidyl-, and p-nitrophenyl- activated esters; acrylates; glycidyl ethers; and aldehydes, and R is a spacer defined as a backbone to which the two polyalkylene arms are attached, consisting preferably of bisphenol A or B. Bisphenol A is preferred, as shown in the structure of FIG. 2.

We have also determined that in certain applications the imidazole derived polyalkylene oxides provide excellent results, perhaps because the reaction proceeds somewhat better, or perhaps because residual unreacted groups improve leukoadhesion. In any event, Applicants do not wish to be bound to any particular theory, but disclose the result as a guide to those experienced in the art. In general, polyalkylene means polyethylene or polypropylene, since these are the most common polyalkylene oxides used in biocompatibility applications. However, Applicants consider other polyalkylene oxides up to polybutylene oxide to be within the scope of the invention.

In an embodiment, a tetra or diacrylate terminal derivative of polyalkylene oxide may be isopolymerized by first contacting with the surface, followed by irradiation with UV light or gamma rays to effect free radical polymerization. When used for blood filtration, the resulting coated filter matrix is leukodepletive with adequate recoveries of platelets and red bloods cells, but is not a efficacious as the other embodiments of the invention set forth herein.

In a method of the present invention, insitu chemical condensation can be carried out to mold the copolymer skin to the contours of the matrix fiber bed. It is important that the electrophilically active polyalkylene oxide be deposited on the matrix first, dried, and then further contracted with the second amino- or hydroxy- containing nucleophilic polymer. This teaching arises from empirical observation as to which method steps give best results in terms of platelet and RBC recovery, and leukodepletion, and the mechanistic or molecular basis for the observation is unknown to Applicants. In the drying step, drying in ambient air is adequate to "fix" the polymer in position, but light to moderate heat at various humidities down to less than 5% humidity or in vacuo may be applied to hasten the drying step in a manufacturing context.

The copolymerized material is highly stable to leaching, as shown in some of the Examples. In contrast to unreacted single polymer labeled with $^{125}$I which is readily leached into filtrate, the fully copolymerized material made according to a method of the present invention is highly resistant to leaching, and is stable for preparation of therapeutically acceptable cell fractions.

By way of example, and not limitation, examples of the present invention will now be given.

EXAMPLE NO. 1

Figures 3A, 3B:
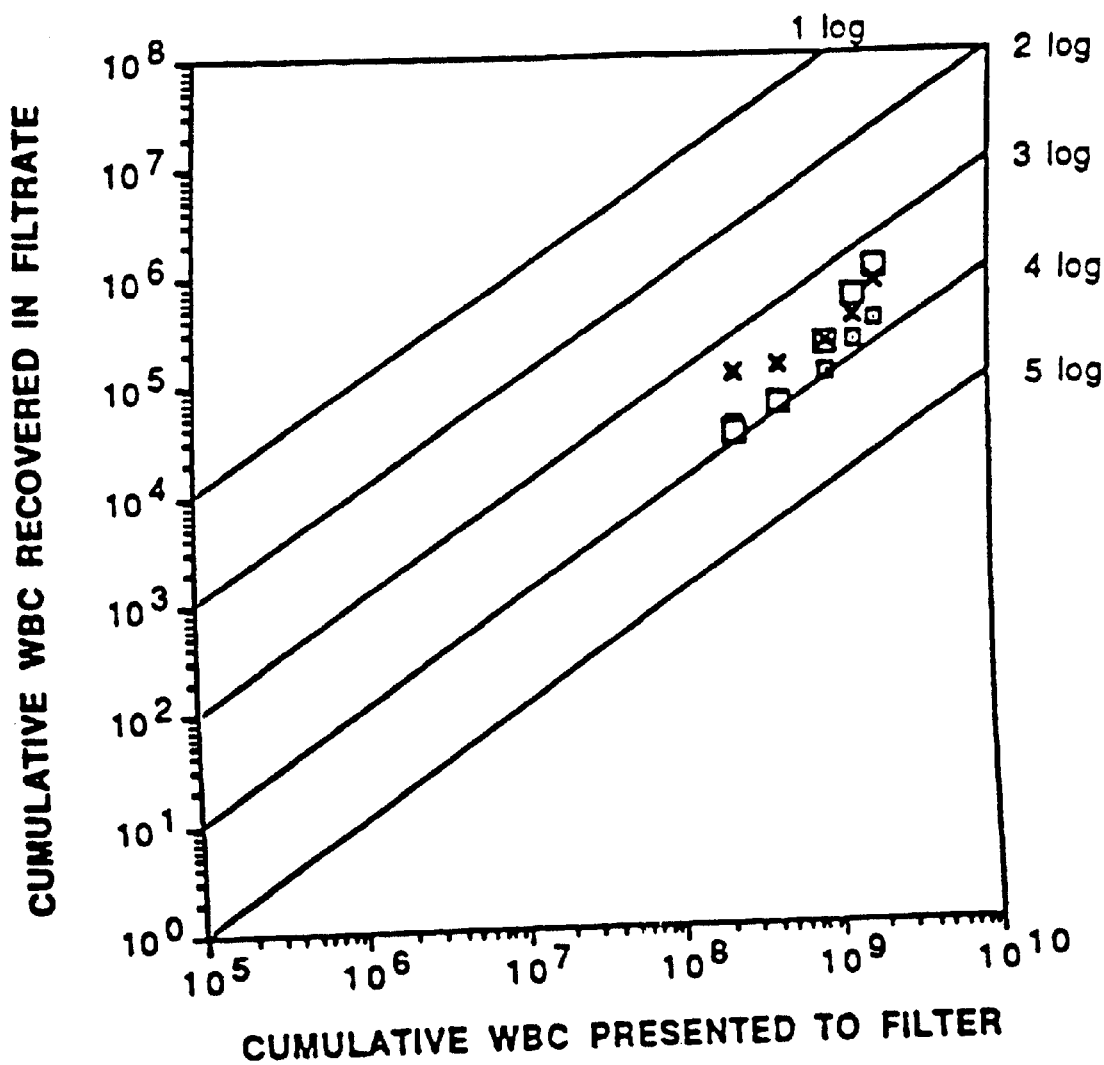
FIG. 3 illustrates the relative WBC depletion for PEO-coated and uncoated Asahi R-2000 filters. Log depletion is illustrated on the right side of the figure.
Figures 4A, 4B:
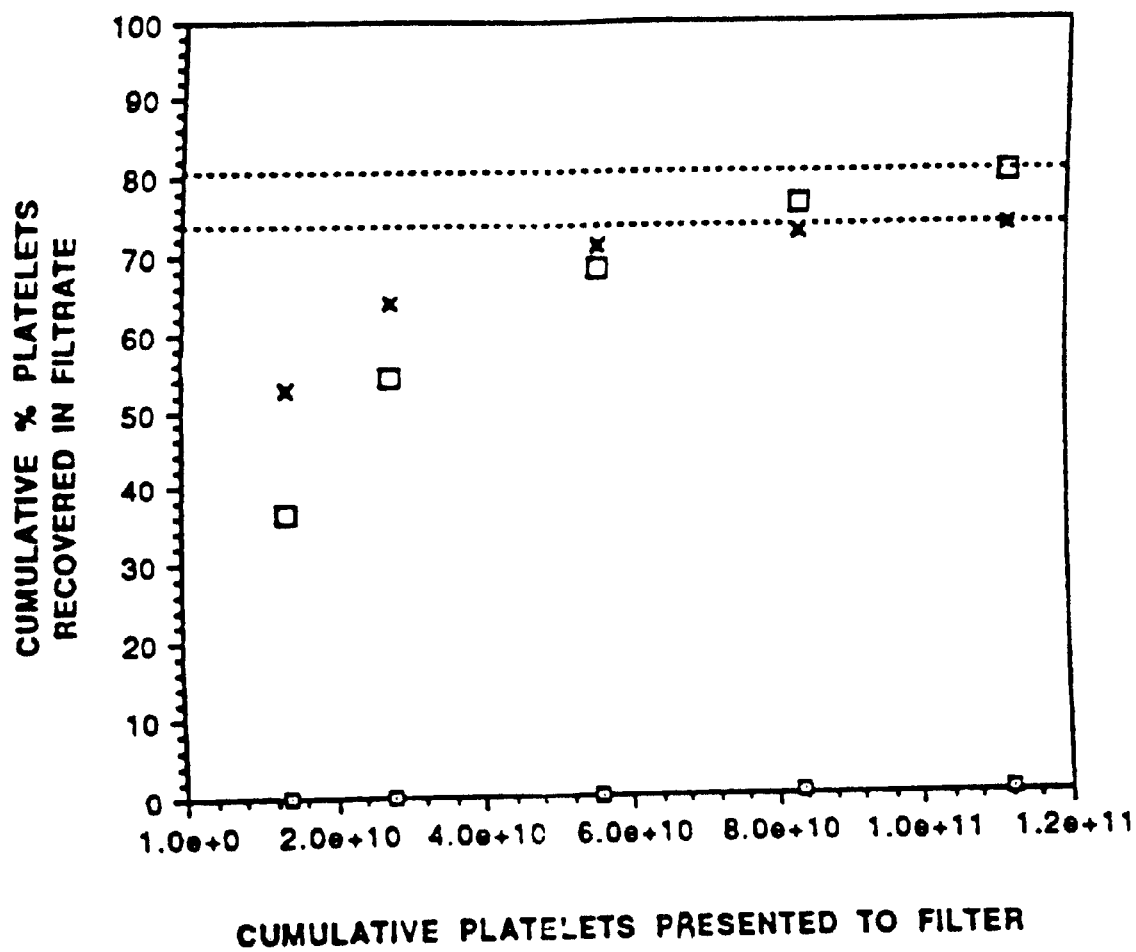
FIG. 4 illustrates the relative platelet recovery obtained with PEO-coated and uncoated Asahi R-2000 filters.

Oxycarbonyl imidazole-polyethylene oxide (Imz-PEO) with an average molecular weight of 20 K daltons (Sigma Chemical Company), was first coated onto existing Asahi R-2000 filters by soaking the filter mats in a 2.5% solution of Imz-PEO. The mats were dried under vacuum. The amount of Imz-PEO bound to the mat was about 70 mg/gram of filter mat. Dried Imz-PEO-coated mats were cross-linked with bis[polyoxyethylene bis(amine)] (TAPEO, 20 K daltons), obtained from Sigma Chemical Company. The cross-linking reaction was performed by soaking the Imz-PEO-coated mat in a water-methanol (1:1) solution of TAPEO at a 2.5 to 5.0 fold molar excess over the bound Imz-PEO. The reaction was allowed to proceed for at least 24 hours. The mats were dried again under vacuum. Dried cross-linked mats were washed extensively by soaking with water several times to remove any unbound PEO. After the final wash, the mats were dried again under a high vacuum. Cross-linked mats were stored at room temperature until used for blood filtration. In this example, the mats were used with pooled (ABO compatible), one day old, human whole blood, obtained from Interstate Blood Bank. The pooled whole blood was suspended about 3 feet above the filter unit, and the blood was allowed to flow by gravity through each of the different types of PEO-filter mats. An aliquot of whole blood (20 to 30 ml) was taken from the unit before filtration and was saved as a control (pre-sample). The filtered blood (post samples) and the pre-samples were counted for platelets with a Sysmex K-1000 cell counter and the WBC concentrations were determined by staining WBC nuclei (after lysing the sample) with propidium iodide and analyzing the stained samples with a FacScan flow cytometer. The results of WBC depletion and platelet recovery are illustrated in FIGS. 3 and 4 respectively. The degree of platelet recovery ranged from 75 to 80% with Imz-PEO-coated mats vs 0.5% for the uncoated mats. The amount of WBC depletion remained unchanged, in the range of 3 to 4 logs for all of the mats (Table 1).

TABLE 1

Filtration of Whole Blood Through PEO-Coated And Uncoated Asahi R-2000 Filter Mats

| SAMPLE | WBC Depletion Depletion (log) | PLATELET Recovery (% Pre) |
|---|---|---|
| Imz-PEG (no crosslinking) | 3.25 | 80 |
| 2.5x Crosslinked (Mat #1) | 3.39 | 74 |
| 2.5x Crosslinked (Mat #1) | 3.75 | 74 |
| Uncoated | 3.73 | 0.5 |

EXAMPLE NO. 2

In this experiment, variable such as the age of the blood and the storage temperature were evaluated. The same PEO coated Asahi R-2000 filter mats described above were used for these studies. Units of whole blood were obtained fresh in-house, and stored at room temperature until used (about 2 hours). One day old blood, stored at room temperature or 4 degrees centigrade, were also obtained form Interstate Blood Bank. Each unit was allowed to flow through each PEO-coated filter and the samples were analyzed as described above. The results, summarized in Table 2, suggest that despite the utilization of various units of whole blood stored under different conditions, the yield of platelets obtained from PEO-coated Asahi R-2000 filters is dramatically improved (68 to 83%) as compared to uncoated mats (2%).

TABLE 2

Filtration Of Whole Blood Through PEO-Coated And Uncoated Asahi R-2000 Filters

| SAMPLE | WBC Depletion (log) | PLATELET Recovery (% Pre) |
|---|---|---|
| PEO-Cross Linked-Mats: | | |
| Interstate-RT (1 day old) #1 | −2.63 | 83 |
| Interstate-RT (1 day old) #2 | −4.01 | 68 |
| Interstate-4° C. (1 day old) #3 | −3.22 | 80 |
| In-house-RT (~2 hrs) #1 | −3.25 | 76 |
| Uncoated Mats: | | |
| Interstate-RT (1 day old) #1 | −3.50 | 02 |

EXAMPLE NO. 3

In this example, tetraacrylate PEO derivatives were obtained either from Shearwater Polymer Inc., or synthesized from PEO 20 K daltons obtained from Sigma (FIG. 2). The acrylate-PEO derivatives were coated onto composite mats by the same procedure as described in Example 1. The dried acrylate-PEO-coated mats were subjected to gamma irradiation at a low dosage (2 megarads) to facilitate cross-linking of the PEO coating. The dried, coated mats were cut into circles of about 1.50 inches, and 3 layers of mats were placed into a small pediatric-sized housing for whole blood evaluation. One day old pooled whole blood, obtained from Interstate Blood Bank was used. The final volume of blood used per housing was about 75 ml. The results of these experiments, summarized in Table 3, demonstrate the improvement in platelet recovery upon coating mats with the PEO derivatives. However, the improvement in platelet recovery seen with the acrylate PEO derivatives is not as good as was observed with the Imz-PEO coated mats.

TABLE 3

Filtration Of Whole Blood Through Various Crylate-PEO-Coated and Uncoated Composite Filters

| SAMPLE | WBC Depletion Depletion (log) | PLATELET Recovery (% Pre) |
|---|---|---|
| Uncoated | −2.20 | 43 |
| Sigma-Tetra-Acrylate-20K | −1.62 | 69 |
| Shearwater-Tetra-ACR-14K | −2.04 | 56 |
| Sigma-Tetra-Acrylate-20K Irradiated | −1.64 | 65 |
| Shearwater-Tetra-ACR-14K Irradiated | −1.91 | 65 |

EXAMPLE NO. 4

The stability of these PEO coatings was investigated using radioactively labeled $^{125}$I-Imz-PEO and $^{125}$I-

Tetraamino-PEO. The presence of the bis phenol A units in the structure of Imz-PEO or Tetraamino-PEO derivatives permitted conventional labeling of these molecules using $^{125}$I and iodo beads (Pierce Chemical Co.). In the first set of experiments, the $^{125}$I-Imz-PEO was first coated onto the mats and was cross-linked with unlabeled Tetraamino-PEO. In the second set of experiments, unlabeled Imz-PEO was coated onto the mats and then cross-linked with $^{125}$I-Tetraamino-PEO. Each $^{125}$I-PEO coated mat was evaluated in a Swinney housing (using a filter about 1 cm in diameter) with fresh whole blood. Four fractions of blood filtrate (~1 ml each) were collected and counted for the presence of $^{125}$I-PEO derivatives with a gamma counter. Each $^{125}$I-PEO-coated filter mat was also counted for radioactivity, before and after filtration. The amount of labeled PEO recovered on the mats after whole blood filtration varied from 87% to 95%. In contrast, 35% of the labeled Imz-PEO was leached off filter mats where no crosslinking reaction was performed.

TABLE 4

Stability Of PEO-Coated Asahi R-2000 Filter Mats Measured With $^{125}$I-Imz-PEO or $^{125}$I-Tetraamino-PEO

| SAMPLE With $^{125}$I-Label | 125I-PEO Coated Mats Recovered After Filtration (% Pre Labeled Mat) |
|---|---|
| 125-Imz-PEO-Tetraamino-PEO | 95% |
| Imz-PEO-125I-Tetraamino-PEO | 87% |
| 125I-Imz-PEO (not cross-linked) | 65% |

EXAMPLE NO. 5

Various pre and post blood samples from the above experiments were further evaluated for complement activation by measuring C3a and C5a (by RIA) and for platelet activation by determining the percentage of platelets positive for the activation marker CD62. PLS10A platelet filters (Asahi) were included in this analysis as a control for comparison. The results for C3a and C5a is summarized in Table 5.

TABLE 5

C3a And C5a Levels In Blood Exposed To PEO-Coated And Uncoated Asahi R-2000 and PLS-10A Filters

| SAMPLE | C3a (ng/ml) Pre-Samples | Post-Samples | C5a (ng/ml) Pre-Samples | Post-Samples |
|---|---|---|---|---|
| Cross-linked | 952 | 1,276 | 20 | 54 |
| Cross-linked | 538 | 614 | 0 | 19 |
| Cross-linked | 857 | 1,047 | 17 | 13 |
| Cross-linked | 1,103 | 1,149 | 28 | 34 |
| Cross-linked | 610 | 619 | 15 | 15 |
| Uncoated | 319 | 248 | 29 | 19 |
| Uncoated | 686 | 716 | 15 | 11 |
| PLS-10A | 964 | 4,057 | 22 | 66 |
| PLS-10A | 839 | 2,169 | 33 | 34 |
| PLS-10A | 328 | 1,727 | 9 | 25 |
| PLS-10A | 437 | 2,572 | 4 | 26 |

High levels of C3a and C5a were found in blood samples obtained from Asahi platelet filter PLS-10A. Although these PLS-10A filters have not been used with whole blood, it appears that the PLS-10A produces at least a 2 to 4 fold increase in C3a and C5a levels as compared to the corresponding pre-samples. These levels of C3a and C5a are higher than the amount of C3a and C5a produced by the PEO-coated Asahi R-2000 filters are more biocompatible than the PLS-10A commercial filter used for platelet concentrate.

The percent of platelets expressing the activation marker, CD62, is a sensitive measure of the extent of platelet activation. Samples of whole blood were analyzed (pre and post filtration) using a FacScan flow cytometer to determine the percentage of platelets positive for CD62. This analysis revealed (Table 6) that no elevation in the percentage of CD62 positive platelets occurred during filtration on any of the mats investigated.

TABLE 6

Platelet Activation In Whole Blood Samples Exposed To Various Filters

| SAMPLE | % CD62 in Pre-Samples | % CD62 in Post-Samples |
|---|---|---|
| Uncoated | 5.45 | 5.88 |
| Cross-linked-PEO | 4.45 | 4.78 |
| Cross-linked-PEO | 5.20 | 5.24 |
| Not Cross-linked-PEO | 5.45 | 3.27 |
| Not Cross-linked-PEO | 4.05 | 2.11 |
| PLS-10A | 5.45 | 2.10 |

EXAMPLE NO. 6

In this group of examples, polyvinyl chloride and silicone tubes were coated.

A. PEO-Coated Polyvinyl Chloride (PVC) Tubes:

PVC tubes (10 or 15 French size) were soaked in a water solution containing various concentrations of $NH_2$-PEO (1%, 2.5% or 5%). The tubes were incubated at 55° C. overnight, then they were removed. The tubes were allowed to air dry at room temperature following by another incubation at 55° C. as the curing process.

The $NH_2$-PEO-coated PVC was either used for crosslinking with another PEO derivative without further washing or was washed extensively with water to remove free PEO. Washed tubes were allowed to air dry at room temperature and stored desiccated until analysis. Note that the amount of bound PEO was estimated based on the amount of radioactive $^{125}$I-labeled-PEO tracer that was incorporated in the PEO coating solution.

B. Cross-Linking Of Amino-PEO-Coated PVC:

Dried $NH_2$-PEO-coated PVC (before washing) was soaked in a water solution containing Imz-PEO at a concentration of 2.5% (or lower). The crosslinking reaction was performed at room temperature for 24 hours.

The tubes were removed and allowed to air dry at room temperature. The tubes were then extensively washed with water to remove free Imz-PEO. The washed tubes were dried at room temperature and stored desiccated as described above.

C. PEO-Coated Silicone Tubes:

Silicone tubes (15 French size) were pre-treated with sodium hydroxide before being treated with a PEO coating. The sodium hydroxide treatment consisted of soaking the tubing in 1N sodium hydroxide for 1 hour, following by extensive washing (until neutral pH) of the tubes with water.

The method of coating PEO derivatives (Imz-PEO or $NH_2$-PEO) onto silicone tubes was the same as for PVC above, except that all soaking in PEO solutions were performed at room temperature. The step that involved curing at 55° C. was omitted. The final washed tubes were stored in a desiccated vacuum.

D. Attachment of Heparin and Imz-PEO onto Silicone Tubes:

Heparin and Imz-PEO can be incorporated into the silicone matrix by either reacting heparin with Imz-PEO-coated silicone tubes (a two step process), or by mixing Imz-PEO and heparin in the same solution that was used as coating solution (a one step process). All heparin attachment was performed at 4° C. for 24 hours. The tubes were dried and washed as described earlier.

E. Fibrinogen Binding Assay:

All PEO or Heparin-PEO-coated tubes were tested for fibrinogen binding against control uncoated tubes. Each assay was performed with a triplicate sample using a small piece of tubing (about 0.4 cm length).

F. Measurement Of Surface Lubricity:

Each tube was cut into about 15 lengths and was placed into a designed flow-cell filled with saline (0.9% solution). One end of the tube was connected to an Instron instrument that served to pull out the tube from the flow-cell. The maximum force required for the Instron to pull the tube out determines the surface lubricity of the tube.

The force used for pulling the control tube (uncoated PVC or silicone) was set at 20 lb. The measurement was performed at two time intervals: 1) at time zero (t=0) where the tube was pulled as soon as it was loaded into the flow-cell; and 2) at rinsed time (t=30 minutes) where the tube was allowed to stay in the flow-cell containing saline solution for 30 minutes. Then, the saline solution in the flow-cell was replaced with new saline, and finally the tube was pulled out.

G. Stability Study of PEO-Coated PVC or Silicone:

This study was performed in saline and plasma solutions, at 37° C. up to 7 days, using $^{125}$Imz-PEO or $^{125}$I-NH$_2$-PEO-coated tubes (the radiolabeled PEO was used as a tracer). Several sets of small pieces (about 0.4 cm length) of $^{125}$I-PEO-coated PVC (or silicone), and uncoated tubes were soaked in saline or pure plasma solutions. The samples were placed on a tube rocker which allows a continuous shaking of the samples during the entire incubation period. Each set of tubes (in triplicate) was removed from the shaker after day-1 (24 hours), day-3, and day-7. Each sample was counted for total radioactivity before removal of saline or plasma solution, then it was washed twice with water. The washed piece was counted for the remaining radioactivity. The ratio between the remaining radioactivity of PEO-coated tubes after washing and the total radioactivity was recorded.

Results

Figure 5:
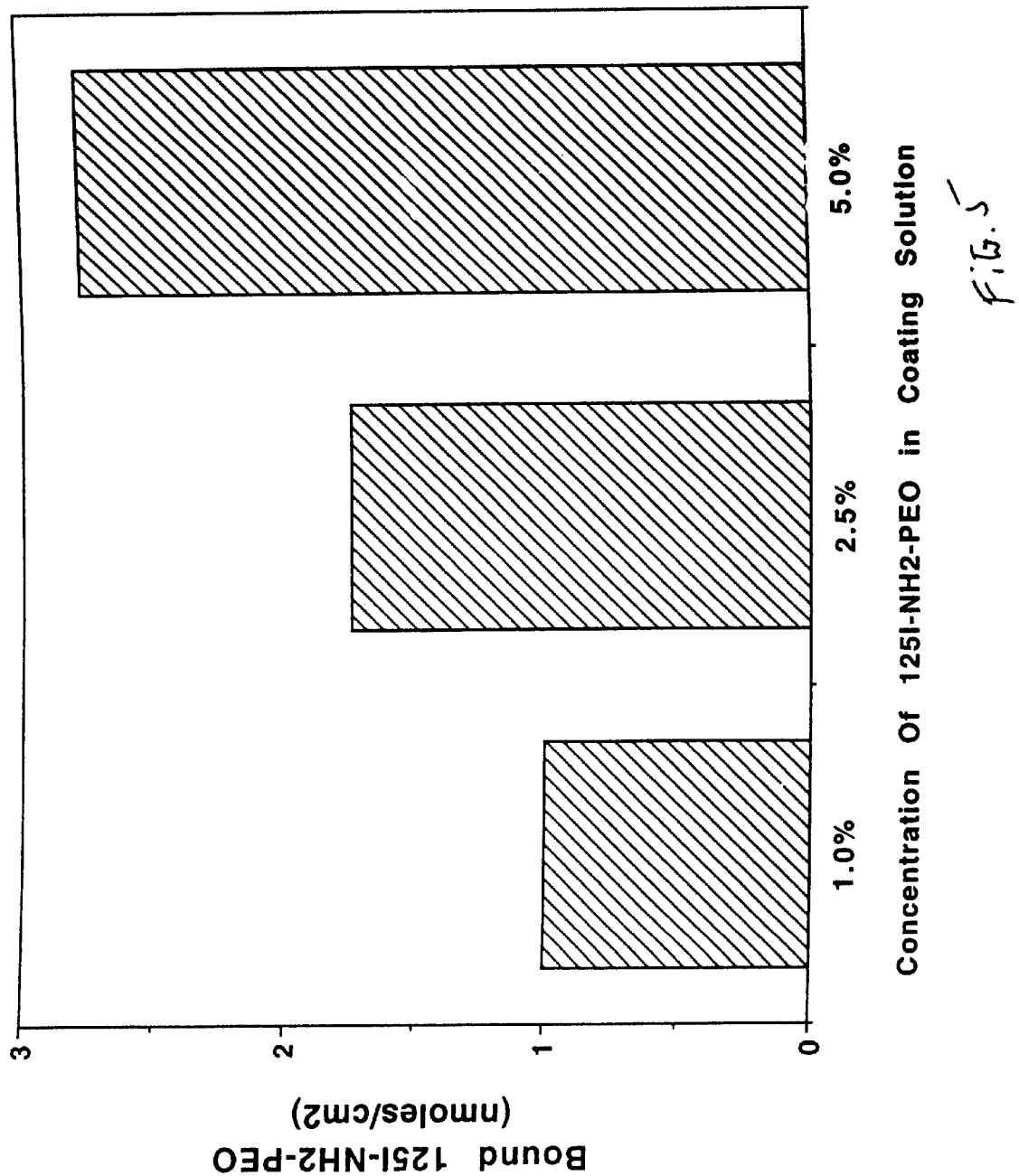
FIG. 5 illustrates the surface lubricity of a PVC tube having a $NH_2$-PEO coating using an Instron instrument test pursuant to Example 6.
Figure 6:
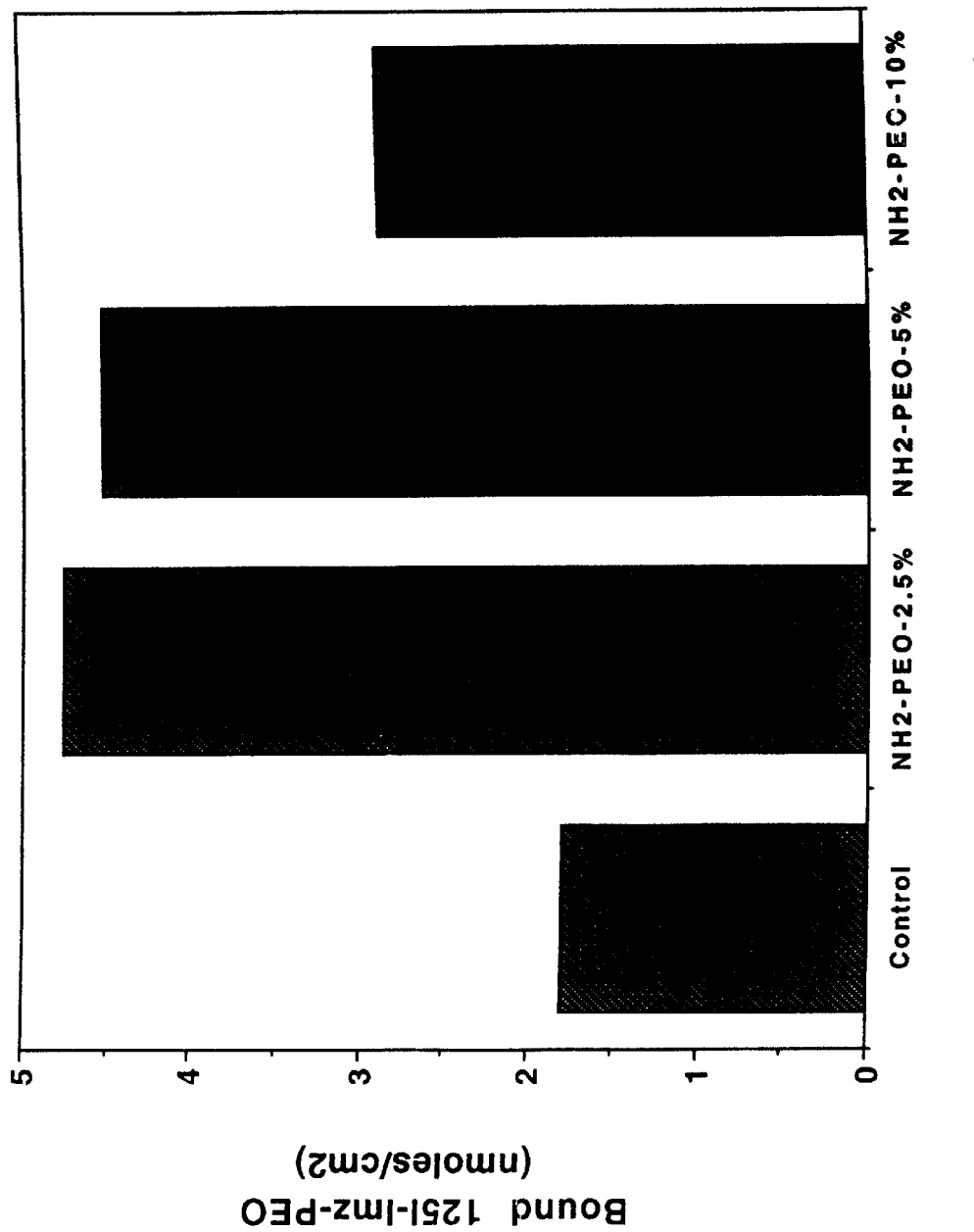
FIG. 6 illustrates the surface lubricity of a tube using an Instron instrument test pursuant to Example 6 for a Imz-PEO coating onto a $NH_2$-PEO coated PVC tubing.

PEO-Coated PVC:

The results of Imz-PEO or NH$_2$-PEO-coated PVC tubes are illustrated graphically in FIGS. 5 and 6. FIG. 5 illustrates graphically bound NH$_2$-PEO (mmoles/cm$^2$) versus NH2-PEO concentration in the coating solution. Three solution concentrations are illustrated: 1.0%; 2.5%; and 5.0%. As shown in FIG. 5, NH$_2$-PEO appeared to bind better to the PVC tubes than the Imz-PEO derivative. Also, the amount of bound NH$_2$-PEO onto PVC increased with increasing concentration of the NH$_2$-PEO in the coating solutions. However, using high concentration of this NH$_2$-PEO (e.g. 10%) in a primary coating solution is not necessary, because it reduced the amount of bound Imz-PEO used in the crosslinked reaction; see FIG. 6, concentration of NH$_2$-PEO in coating solution (before cross-linking).

Figure 7:
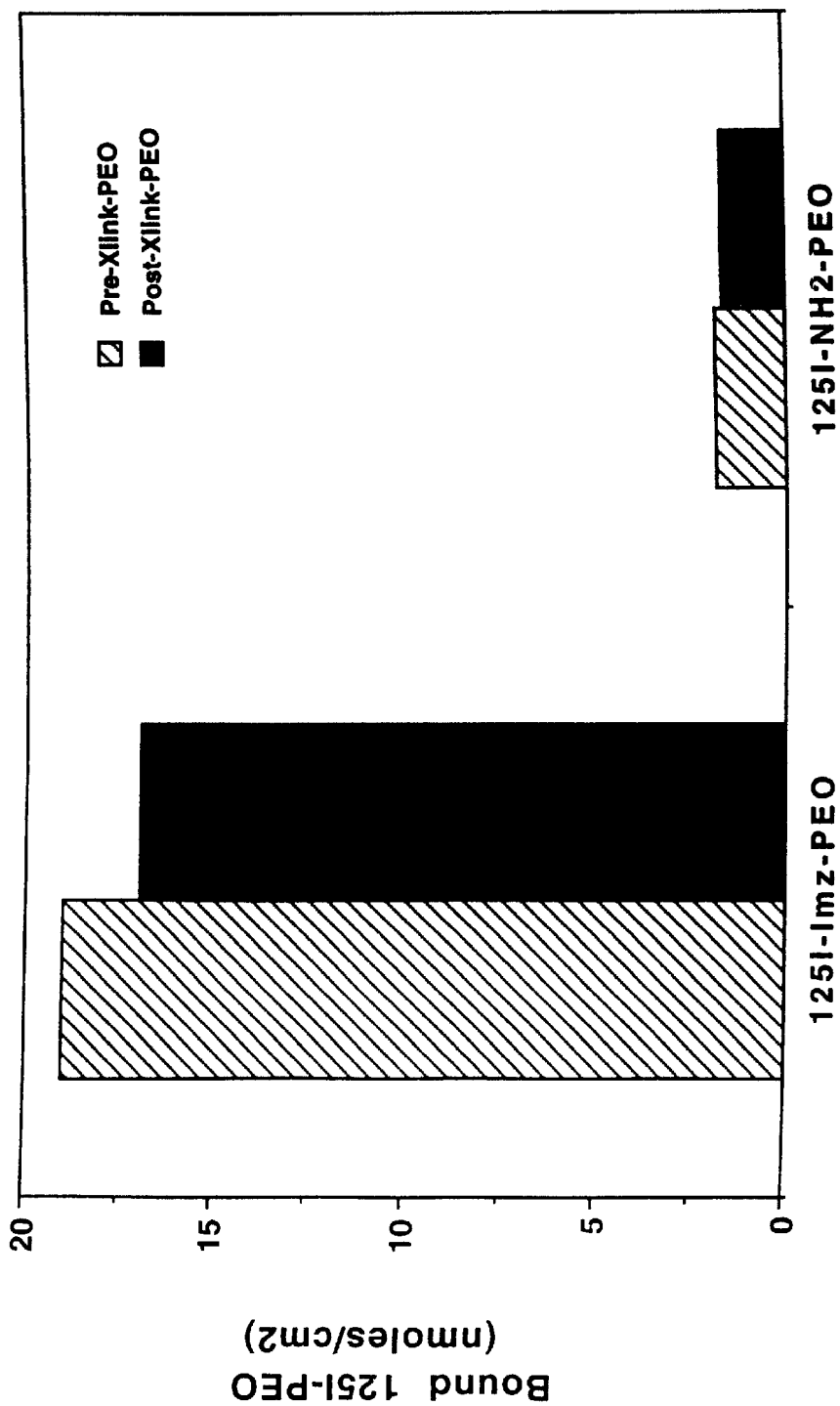
FIG. 7 illustrates the surface lubricity of a tube using an Instron instrument test pursuant to Example 6 for a Imz-PEO coating and a $NH_2$-PEO coating on a silicone tubing.

PEO-Coated Silicone:

FIG. 7 sets forth two PEO derivatives: Imz-PEO (Imz-PEO cross-linked with NH$_2$-PEO); and NH$_2$-PEO (NH$_2$-PEO cross-linked with Imz-PEO). Illustrated in FIG. 7, both PEO derivatives were strongly bound to silicone tubing. The amount of Imz-PEO bound was about 4 fold higher than the amount of bound NH$_2$-PEO. In addition, the results in FIG. 6 suggested that the primary coating of PEO was very stable since the level of radioactivity was unchanged after the crosslinking reaction.

Fibrinogen Binding:

The results of fibrinogen binding to PEO-coated PVC tubing are summarized in Tables 7 and 8 below.

As shown in Table 7, PEO-coated PVC exhibited a great reduction in fibrinogen binding, compared to control uncoated PVC. Tubings coated with a low concentration of NH$_2$-PEO (1%) showed the same level of bound fibrinogen, compared to other tubings that were coated with higher concentrations of NH$_2$-PEO (2.5% or 5%), and with or without crosslinking with Imz-PEO (Table 7).

TABLE 7

Effect Of PEO Coating On Fibrinogen Binding Onto PVC Tubing

| [NH$_2$-PEO] in coating solution | Bound Fg (ng/cm$^2$) before crosslinked (± SD) | Bound Fg (ng/cm$^2$) after crosslinked (± SD) |
| --- | --- | --- |
| Uncoated | 670 ± 124 | |
| 1% | 85 ± 9 | 136 ± 23 |
| 2.5% | 110 ± 7 | 110 ± 19 |
| 5.0% | 114 ± 27 | 127 ± 20 |

Also, the results in Table 8 indicated that there was no change in the level of fibrinogen binding to the PVC tubing after ETO sterilization.

TABLE 8

Effect Of ETO Sterilization On Fibrinogen Binding to PEO-Coated PVC Tubing

| PVC Tubing | Bound Fg (ng/cm$^2$) before ETO (± SD) | Bound Fg (ng/cm$^2$) after ETO (± SD) |
| --- | --- | --- |
| Uncoated | 462 ± 43 | 394 ± 65 |
| NH$_2$-PEO (1%) | 80 ± 19 | 82 ± 26 |
| Xlink-PEO (0.5% Imz-PEO) | 84 ± 20 | 27 ± 15 |
| Xlink-PEO (2.5% Imz-PEO) | 69 ± 22 | 46 ± 8 |

The ability of the PEO coating to reduce fibrinogen binding was also demonstrated to be obtained with silicone (see Table 9 below). The level of fibrinogen bound to the Imz-PEO or NH$_2$-PEO-coated silicone with or without crosslinking was about the same. This result suggests that the second crosslinking reaction with Imz-PEO derivative may not be necessary in this type of coating.

TABLE 9

Effect of PEO Coating On Fibrinogen Binding Onto PVC Tubing

| Silicone Tubing & PEG Coating | Bound Fg (ng/cm$^2$) Pre-Crosslinked (± SD) | Bound Fg (ng/cm$^2$) Post-Crosslinked (± SD) |
| --- | --- | --- |
| Uncoated | 258 ± 173 | |
| $^{125}$I-Imz-PEO | 82 ± 27 | 52 ± 8 |
| $^{125}$I-NH$_2$-PEO | 62 ± 19 | 46 ± 2 |

Figure 8:
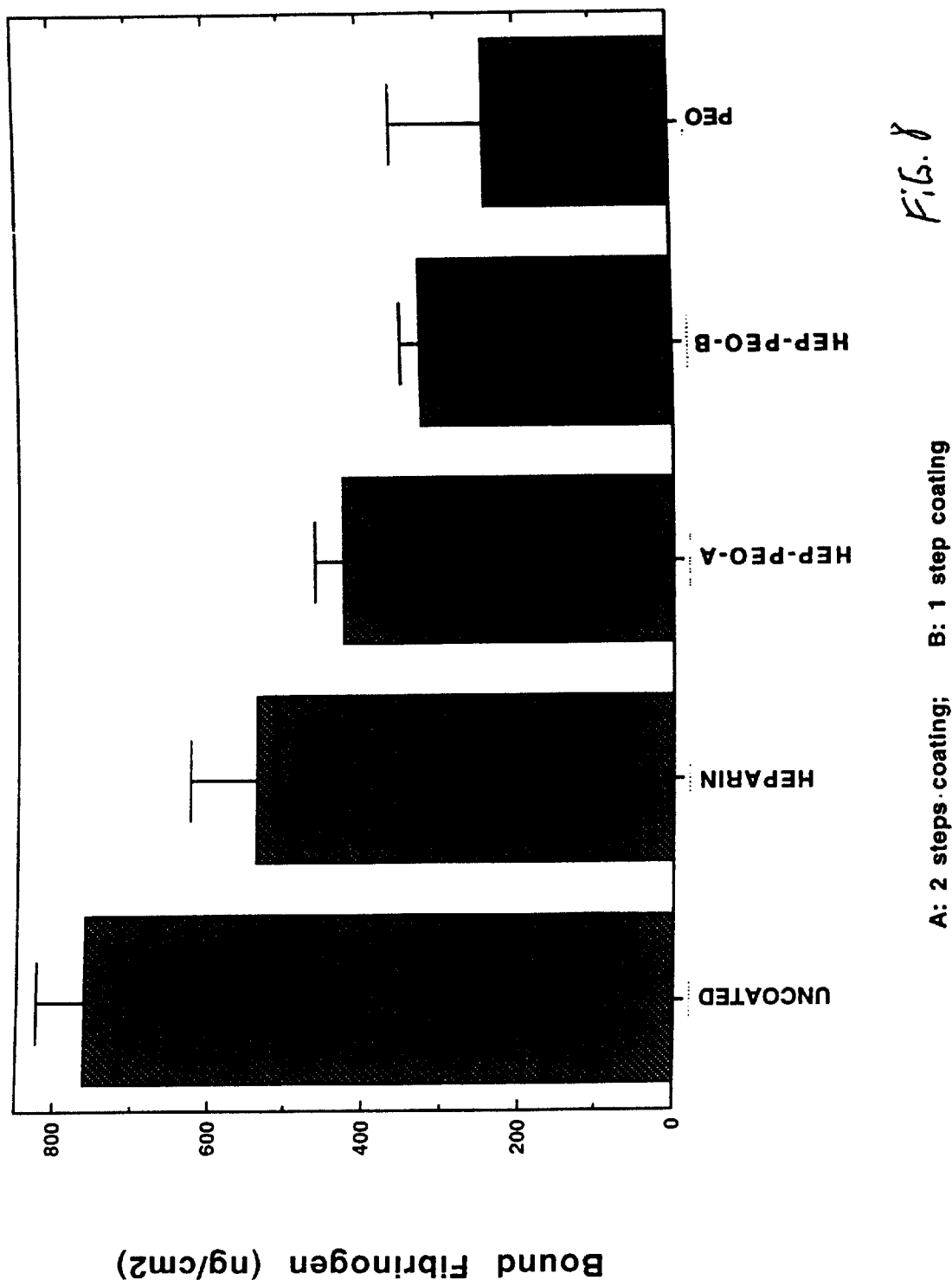
FIG. 8 illustrates graphically the effect of heparin coating on fibrinogen binding to various treated silicone tubings pursuant to Example 6.

However, Imz-PEO coating may be used as crosslinker reagent to the attachment of heparin, as shown in FIG. 8. The results in FIG. 8, indicated that heparin and Imz-PEO can be incorporated onto silicone tubing by a one step (S1) or two step (S2) processes to produce low fibrinogen binding surface. The activity of immobilized heparin is under investigation.

Surface Lubricity:

The results of the effect of PEO coating on tubing lubricity are summarized in Tables 10 and 11 below for PVC and silicone, respectively.

In this analysis, surface lubricity was measured by applying a maximum force to pull out the tube from the flow-cell filled with saline solution. The force for the control uncoated was set at 20 lb, on the Instron instrument.

TABLE 10

Effect Of PEO-Coated PVC On Tubing Lubricity

| PVC (10 fr.) | Pre-ETO (t = 0) | Pre-ETO (t = 30 min.) | Post-ETO (t = 0) | Post-ETO (t = 30 min.) |
|---|---|---|---|---|
| Experiment #1 (n = 3) NH2-PEO (1%) | not done | 7.6 ± 4.3 | not done | 2.6 ± 0.6 |
| Experiment #2 (n = 1) S1(NH2-PEO 1%) | 0.75 | 0.56 | 0.89 | 0.94 |
| S2(Xlink-PEO) (Imz-PEO = 0.5%) | 1.71 | 0.77 | 1.38 | 2.27 |
| S3 (Xlink-PEO) (Imz-PEO = 2.5%) | 0.78 | 0.44 | 0.41 | 0.59 |

TABLE 11

Effect Of PEO-Coated Silicone On Tubing Lubricity Measured by friction test. Control uncoated = 20 lb

| Silicone (15 fr.) (n = 2) | (t = 0) | (t = 30 min.) |
|---|---|---|
| Imz-PEO | 13.6 ± 9.0 | 4.4 ± 1.3 |
| NH2-PEO | 5.7 ± 3.4 | 2.4 ± 0.2 |
| ImzPEO-Xlink | 5.0 ± 0.6 | 2.9 ± 0.3 |
| NH2-PEO-Xlink | 10.8 ± 0.9 | 5.3 ± 0.4 |

The forces required for pulling the PEO-coated PVC or silicone tube were much lower than the force necessary for the uncoated materials. For both initial force (t=0) or rinsed force (t=30 minutes) PVC tubing coated with 1% $NH_2$-PEO solution showed the same degree of lubricity, compared to other coatings (Table 10). These results suggest that $NH_2$-PEO can be used at low concentration (1%) as a single coating onto PVC tubing.

Similar results were also observed with $NH_2$-PEO-coated silicone tubing (Table 11). This derivative by itself can be used alone for coating silicone tube to produce surface with low-friction and low fibrinogen binding.

Stability of PEO Coating:

A. PVC Tubing: The results of the stability study of PEO-coated PVC tubing in saline and in plasma are summarized in Tables 12 and 13, respectively. As set forth in Table 12, all PEO-coated PVC with or without additional cross linking are very stable in saline solution, at 37° C. up to 7 days.

TABLE 12

Stability of $^{125}$I-PEO-Coated PVC Tubing in Saline Solution at 37° C.

| PVC Tubing | % Of Recovery Day-1 (±SD) | % Of Recovery Day-3 (±SD) | % Of Recovery Day-7 (±SD) |
|---|---|---|---|
| [125]I-$NH_2$-PEO-1.0% | 95 ± 9 | 90 ± 9 | 98 ± 2 |
| [125]I-$NH_2$-PEO-2.5% | 94 ± 7 | 94 ± 3 | 93 ± 5 |
| [125]I-$NH_2$-PEO-5.0% | 91 ± 6 | 93 ± 4 | 96 ± 3 |
| Crosslink-1.0% | 92 ± 5 | 102 ± 3 | 92 ± 5 |
| Crosslink-2.5% | 94 ± 8 | 98 ± 4 | 95 ± 4 |
| Crosslink-5.0% | 97 ± 4 | 97 ± 5 | 100 ± 7 |

Also, these tubings (post saline incubation) showed very good reduction in fibrinogen binding compared to control uncoated tubing (see Table 13 below).

TABLE 13

Stability of $^{125}$I-PEO-Coated PVC Tubing in Saline Solution at 37° C.: Effect On Fibrinogen Binding

| PVC Tubing | Bound Fg (ng/cm2) Day-1 (±SD) | Bound Fg (ng/cm2) Day-3 (±SD) | Bound Fg (ng/cm2) Day-7 (±SD) |
|---|---|---|---|
| Uncoated | 576 ± 45 | 513 ± 53 | 561 ± 44 |
| [125]I-$NH_2$-PEO-1.0% | 75 ± 9 | 76 ± 16 | 71 ± 13 |
| [125]I-$NH_2$-PEO-2.5% | 119 ± 20 | 100 ± 25 | 100 ± 18 |
| [125]I-$NH_2$-PEO-5.0% | 87 ± 9 | 101 ± 8 | 93 ± 19 |
| Crosslink-1.0% | 73 ± 10 | 66 ± 11 | 73 ± 18 |
| Crosslink-2.5% | 98 ± 6 | 85 ± 2 | 95 ± 9 |
| Crosslink-5.0% | 86 ± 16 | 79 ± 7 | 92 ± 25 |

However, in pure human plasma, the percentage of the recovery of bound $NH_2$-PEO is in the range of 60% to 90% depend on the initial coating concentrations and the duration of the incubation (see Table 14 below).

TABLE 14

Stability Of $^{125}$I-PEO-Coated PVC Tubing in Human Plasma at 37° C.

| PVC Tubing | % Of Recovery Day-1 (±SD) | % Of Recovery Day-3 (±SD) | % Of Recovery Day-7 (±SD) |
|---|---|---|---|
| [125]I-$NH_2$-PEO-1.0% | 92 ± 2 | 77 ± 10 | 65 ± 5 |
| [125]I-$NH_2$-PEO-2.5% | 86 ± 5 | 77 ± 20 | 72 ± 1 |
| [125]I-$NH_2$-PEO-5.0% | 102 ± 27 | 79 ± 5 | 72 ± 4 |
| Crosslink-1.0% | 95 ± 4 | 91 ± 19 | 75 ± 3 |
| Crosslink-2.5% | 91 ± 1 | 82 ± 6 | 77 ± 6 |
| Crosslink-5.0% | 92 ± 2 | 82 ± 2 | 80 ± 7 |

B. Silicone Tubing: Similar results were obtained with PEO-coated silicone tubing.

In saline the coating is very stable, the percentage of PEO recovery was all above 95% (see Table 15 below).

TABLE 15

Stability Of $^{125}$I-PEO-Coated Silicone Tubing in Saline Solution at 37° C.

| Silicone Tubing | % Of Recovery Day-1 (±SD) | % Of Recovery Day-3 (±SD) | % Of Recovery Day-7 (±SD) |
|---|---|---|---|
| [125]I-$NH_2$-PEO | 101 ± 1 | 102 ± 3 | 102 ± 5 |
| [125]I-Imz-PEO | 100 ± 1 | 100 ± 6 | 99 ± 5 |
| [125]I-$NH_2$-PEO-Crosslink | 98 ± 4 | 94 ± 6 | 92 ± 5 |
| [125]I-Imz-PEO-Crosslink | 93 ± 4 | 98 ± 3 | 88 ± 8 |

After saline incubation, all PEO-coated silicone tubing still showed good reduction in fibrinogen binding (see Table 16 below).

TABLE 16

Stability Of $^{125}$I-PEO-Coated Silicone Tubing in Saline Solution at 37° C.: Effect On Fibrinogen Binding

| Silicone Tubing | Bound Fg (ng/cm2) Day-1 (±SD) | Bound Fg (ng/cm2) Day-3 (±SD) | Bound Fg (ng/cm2) Day-7 (±SD) |
| --- | --- | --- | --- |
| $^{125}$I-NH$_2$-PEO | 84 ± 21 | 68 ± 24 | 89 ± 17 |
| $^{125}$I-Imz-PEO | 103 ± 43 | 99 ± 57 | 102 ± 7 |
| $^{125}$I-NH$_2$-PEO-Crosslink | 70 ± 18 | 50 ± 17 | 55 ± 16 |
| $^{125}$I-Imz-PEO-Crosslink | 99 ± 36 | 79 ± 4 | 86 ± 13 |

In plasma and up to 7 days incubation at 37° C., PEO-coated silicone tubes are very stable, since the percent recovery of bound PEO varied between 80 and 100% (see Table 17 below).

TABLE 17

Stability Of $^{125}$I-PEO-Coated Silicone Tubing in Human Plasma at 37° C.

| Silicone Tubing | % Of Recovery Day-I (±SD) | % Of Recovery Day-3 (±SD) | % Of Recovery Day-7 (±SD) |
| --- | --- | --- | --- |
| $^{125}$I-NH$_2$-PEO | 84 ± 2 | 84 ± 7 | 80 ± 7 |
| $^{125}$I-Imz-PEO | 99 ± 3 | 94 ± 1 | 91 ± 4 |
| $^{125}$I-NH$_2$-PEO-Crosslink | 94 ± 5 | 94 ± 6 | 89 ± 10 |
| $^{125}$I-Imz-PEO-Crosslink | 101 ± 4 | 95 ± 3 | 97 ± 3 |

EXAMPLE NO. 7

A. Cross-linked-PEO-Coated Tissues:

Various Denacol pre-treated bovine pericardium heart valve tissues (HVT obtained from Baxter Edwards) were washed several times with deionized water, cut into circles, and pre-coated with an Imz-PEO solution. This was followed by a reaction with NH$_2$-PEO, at room temperature.

B. Fibrinogen Adsorption:

PEO-coated and uncoated tissues were soaked in a citrate phosphate buffer solution (pH 7.4) containing $^{125}$I-fibrinogen, and incubated at 37° C. for one hour. Unbound protein was removed by washing extensively with PBS, saline and water. The amount of fibrinogen that was bound was calculated from the specific activity of the labeled protein and expressed as nanogram of fibrinogen per surface area.

C. Avidin Cross-linking to Imz-PEO-Coated-Materials:

PVDF flat sheet membranes (or biological tissues) were cut into circles, pre-coated with Imz-PEO, and followed by reaction with Avidin, as described with NH$_2$-PEO above.

D. Coupling of Avidin-PEO-coated Tissue to LC-Biotin-HSA:

Avidin-PEO-coated PVDF, Uncoated PVDF (Millipore) and Avidin-PVDF (with Avidin non specifically bound) were soaked in PBS (pH 7.4) containing LC-Biotin-$^{125}$1-HSA. The LC-Biotin-$^{125}$I-HSA was prepared by coupling NHS-LC-biotin to $^{125}$I-HSA. Unbound HSA-biotin was washed away with PBS and water. The amount of bound HSA was expressed as cpm per surface area.

Figure 9:
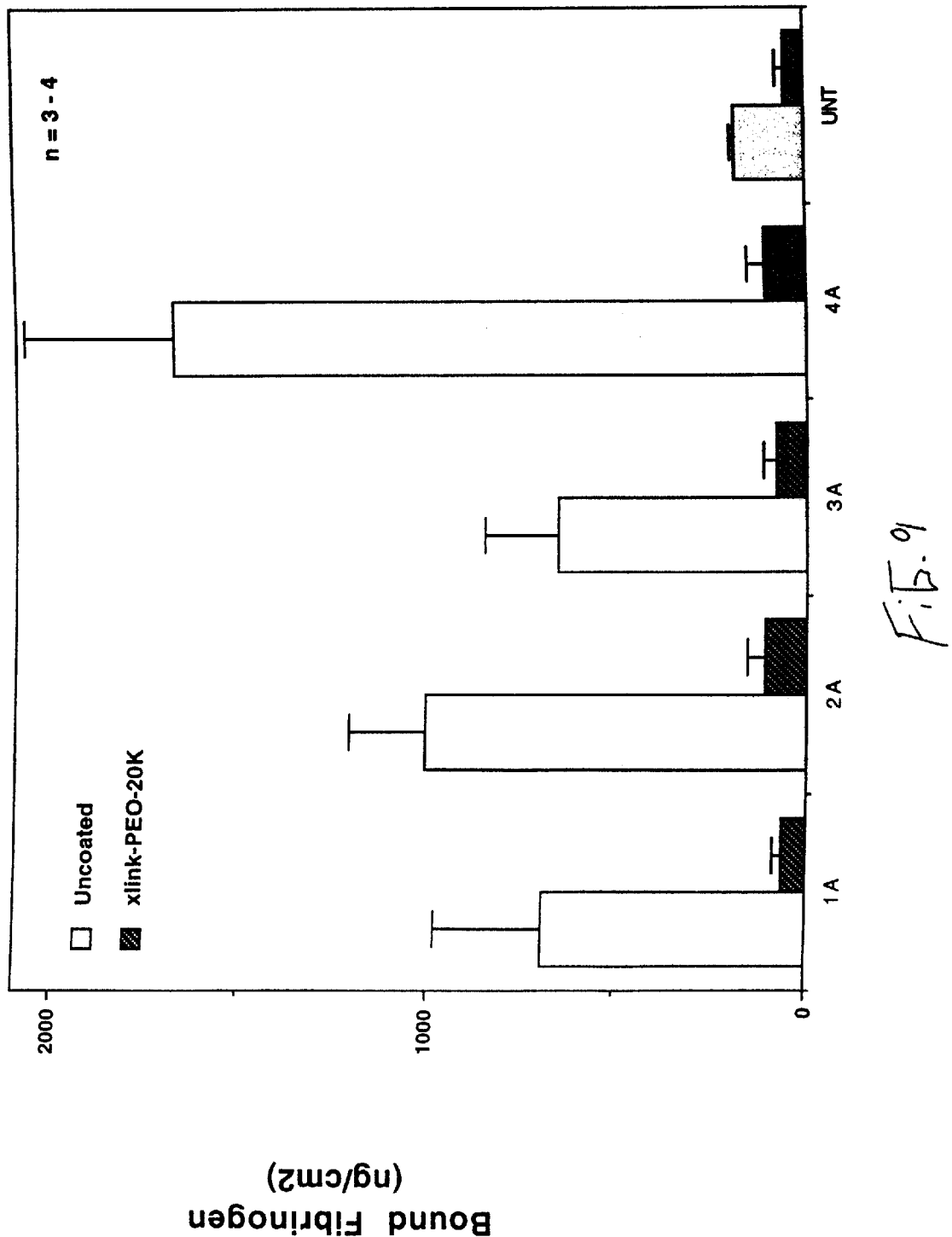
FIG. 9 illustrates graphically the effect of PEO coating on fibrinogen absorption into various HVT pursuant to Example 7.

E. Results:

The results are all illustrated graphically in FIG. 9. These results indicate that all cross-linked-PEO-coated tissues (1A, 2A, 3A, 4A) exhibit about 10 fold lower fibrinogen binding than the corresponding tissues without PEO coating.

Figure 10:
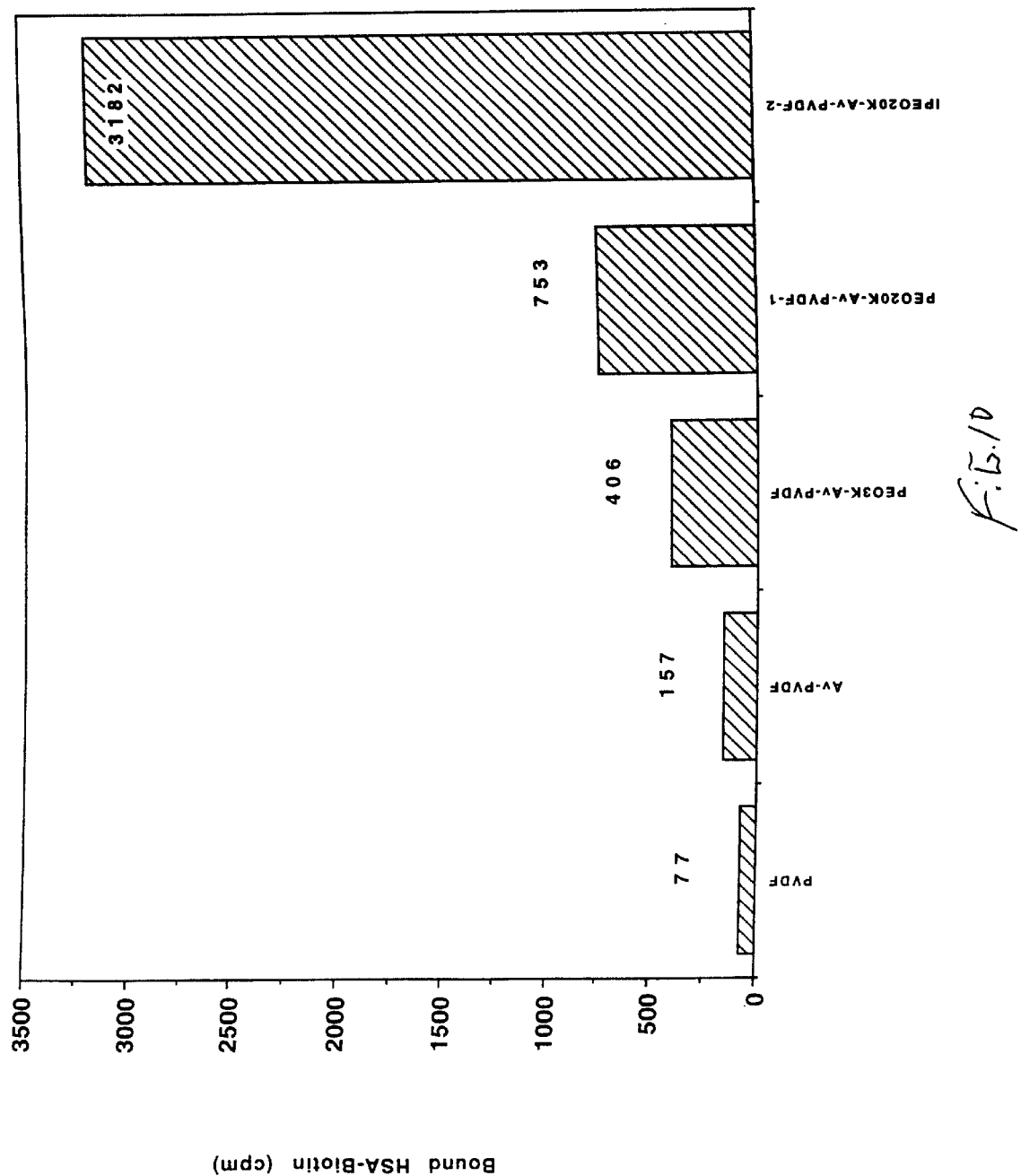
FIG. 10 illustrates graphically the binding of HSA-LC-Biotin to Avidin-coated PVDF with and without pretreatment with Imz-PEO pursuant to Example 7.

FIG. 10 illustrates graphically the binding of HSA-LC-Biotin to Avidin-coated PVDF with and without pre-treatment with Imz-PEO.

The results of the binding of biotin-HSA to Avidin-PEO-coated PVDF membrane, FIG. 10, suggest that Avidin can be covalently attached to the Imz-PEO-coated PVDF to improve the binding of Biotin-HSA, compared to Avidin-coated membranes without PEO treatment.

EXAMPLE NO. 8

A. Cross-Linked Glutaraldehyde-Treated Tissues:

Glutaraldehyde pre-treated bovine pericardium heart valves tissues were washed several times with de-ionized water, and pre-treated with an Imz-PEO solution. This was followed by a reaction with NH$_2$-PEO, at room temperature. The reaction with NH$_2$-PEO may be optional. The result is bovine pericardium tissue treated with PEO.

"Treated" in this sense is considered broader than "coated", as the PEO will tend to diffuse into the tissue rather than merely collecting on the surface. Optionally, the tissue may further be treated with a biologically active recognition sequence, peptide, or compound during or after the reaction with NH$_2$-PEO.

B. Fibrinogen Adsorption:

PEO-treated and untreated tissues were soaked in a citrate phosphate buffer solution (pH 7.4) containing $^{125}$I-fibrinogen, and incubated at 37° C. for one hour. Unbound protein was removed by washing extensively with PBS, saline and water. The amount of fibrinogen that was bound was calculated from the specific activity of the labeled proteins and expressed as nanogram of fibrinogen per surface area.

C. Calcification Assessment:

8 mm disks of PEO-treated and untreated tissues were implanted into the paravertebral muscle of New Zealand albino (NZA) rabbits. After 30 and 90 days implantation, the disks were removed and their calcium was quantified by using known standards, and the results calculated as μg Ca/mg dry weight tissue.

D. Results

The fibrinogen binding results are provided in Table 18 below. These results indicate that cross-linked PEO-treated tissues exhibit about six-fold lower fibrinogen binding than the corresponding tissues without PEO treatment.

TABLE 18

Fibrinogen Binding of both PEO-Treated and Untreated Glutaraldehyde-Fixed Tissue

| Bovine Pericardial Tissue | Bound Fibrinogen |
| --- | --- |
| Untreated | 155 ± 43 |
| PEG-Treated | 24 ± 3 |

Table 19 (below) sets forth the results of the calcium content of a number of explanted PEO-treated tissues at 30 and 90 days. It is apparent that the average for the three given samples at 30 days is skewed by the second tissue explant, and it is believed that the first and third tissue explants are more representative. This is borne out by the more closely grouped results for the three samples at 90 days.

In comparison, the results for a number of control samples is provided in Table 20 (below). The control samples are glutaraldehyde-treated tissues also implanted in the paravertebral muscle of NZA rabbits. The results show that the calcium content of PEO-treated tissues is reduced significantly compared to glutaraldehyde controls. Indeed, even taking into account the seemingly anomalous second PEO-treated tissue sample, the average calcium uptake of the PEO-treated tissues was about one-fifth that of the untreated tissues at 30 days. The difference at 90 days is even more stark, with the average calcium uptake of PEO-treated tissues being about 3% of that of the untreated tissues.

TABLE 19

Calcium Uptake of PEO-Treated Lutaraldehyde-Fixed Tissue from Rabbit Intramuscular Implant Technique

| Rabbit # | Sample # | Time (days) | Total μg/mg Ca | Average ± St. Dev. |
|---|---|---|---|---|
| 703S | B2613-05/4 | 30 | 2.648 | 23.209 ± 36.581 |
| 705S | B2613-05/2 | 30 | 65.445 | |
| 707S | B2613-05/1 | 30 | 1.535 | |
| 697S | B2613-05/4 | 90 | 3.41 | 6.691 ± 5.359 |
| 699S | B2613-05/2 | 90 | 3.788 | |
| 701S | B2613-05/1 | 90 | 12.876 | |

TABLE 20

Calcium Uptake of Untreated Glutaraldehyde-Fixed Tissue from Rabbit Intramuscular Implant Technique

| Rabbit # | Sample # | Time (days) | Total μg/mg Ca | Average ± St. Dev. |
|---|---|---|---|---|
| 703S | B2613-07/5 | 30 | 109.149 | 108.182 ± 32.173 |
| 704S | B2613-07/6 | 30 | 82.031 | |
| 705S | B2613-07/3 | 30 | 73.746 | |
| 706S | B2613-07/3 | 30 | 152.983 | |
| 707S | B2613-07/2 | 30 | 139.964 | |
| 708S | B2613-07/1 | 30 | 91.218 | |
| 697S | B2613-07/5 | 90 | 267.791 | 251.114 ± 32.753 |
| 698S | B2613-07/6 | 90 | 257.285 | |
| 699S | B2613-07/3 | 90 | 267.831 | |
| 700S | B2613-07/3 | 90 | 210.112 | |
| 701S | B2613-07/2 | 90 | 212.551 | |
| 702S | B2613-07/1 | 90 | 291.111 | |

It should be noted that the implant methodology wherein the tissues are implanted in the muscles of rabbits, or of other mammals, is believed to be more effective than traditional subcutaneous implant techniques. That is, tissue implanted subcutaneously tends to become rapidly encapsulated by the host's natural immune response. Because of this encapsulation, and because of the relatively low presence of calcium in such interstitial body spaces, the calcium uptake is from passive diffusion and is thus relatively slow. Therefore, tissue explanted at 30, 60, and even 90 days tends to have a calcium content of around 1 micrograms per milligram dry weight tissue. Differentiating between different tissues samples is thus problematic because of the relatively low resolution of the subcutaneous technique.

Implanting the tissues directly into the animal's muscle, however, vastly increases the exposure of the tissue to body calcium. It is well known that calcium flux within muscles is one of the prime physiological causes of muscle contraction. Therefore, tissue implanted into the muscle is regularly exposed to transitory calcium flows. Because of the increased calcium exposure, the tissue more rapidly absorbs the calcium, and thus exhibits a much higher calcium content at 30, 60 and 90 days. The sensitivity or resolution of this implant methodology greatly facilitates differentiation and analysis of the results for different tissue specimens.

A full disclosure of the muscle implant methodology is provided in co-pending U.S. patent application Ser. No. 09/387,468, entitled "In vivo Screening Methods for Predicting Calcification of Implantable Prosthetic Material" filed on even date herewith.

It should also be noted that the PEO treatment as disclosed herein may be effective in tissues other than bovine pericardium. For example, allograft tissue, porcine tissue, equine tissue, or other xenograft tissue may be treated with PEO to obtain the benefits mentioned herein, in particular calcification mitigation. In addition, although PEO treatment has been tested on tissue that has first been pre-treated, or cross-linked, with Denacol or glutaralddehyde, the same benefits described herein may also be obtained by treating fresh tissue.

EXAMPLE NO. 9

In this example, methods and samples having multiple coatings were prepared and tested.

A. PEO-coated Chitosan Surfaces:

1. Attachment of PEO onto Chitosan-mats:

Glass filter mats (GFM) were cut into circles (about 1 cm in diameter). The circles were first modified with 1% chitosan solution. The PEO derivatives with various lengths (PEO-5K, PEO-18.5K and PEO-20K) were then covalently attached to the mats through the amine functional group of the chitosan ligand. At the end of the coupling reaction, some mats were treated with an NHS-acetate to acetylate the unreacted amine groups of the chitosan polymer.

2. Evaluation with Whole Blood:

Citrated, fresh whole blood was filtered through various PEO-coated chitosan mats and uncoated chitosan-mats. Fractions of 1.0 ml (×2) were collected as post-samples. The number of white blood cells (WBC) and platelets were determined on the pre-samples and post samples using a Sysmex cell counter.

Figure 11:
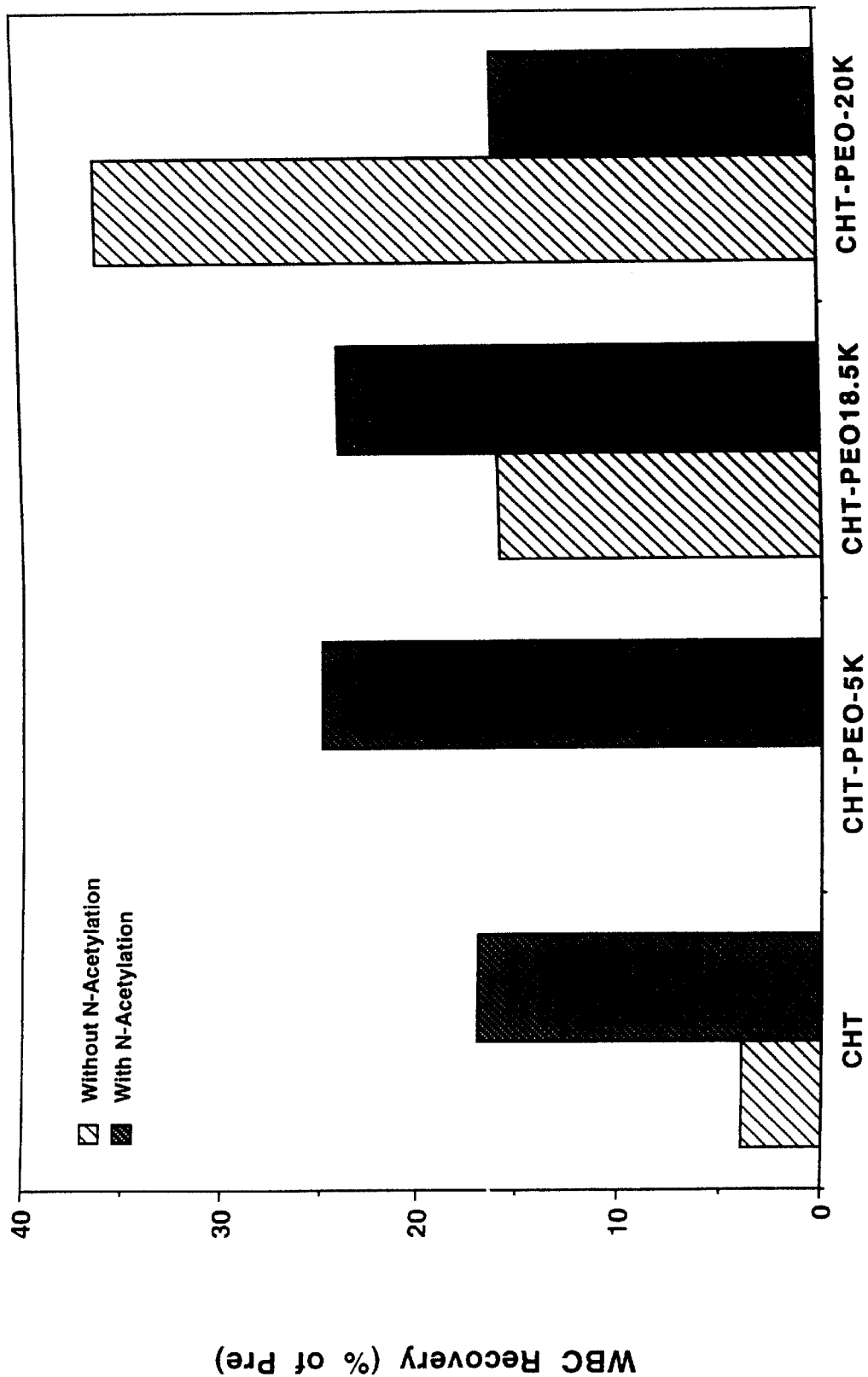
FIG. 11 illustrates graphically PEO coating on chitosan-treated glass filter mats with and without N-acetylation and the effect on WBC recovery from whole blood pursuant to Example 8.
Figure 12:
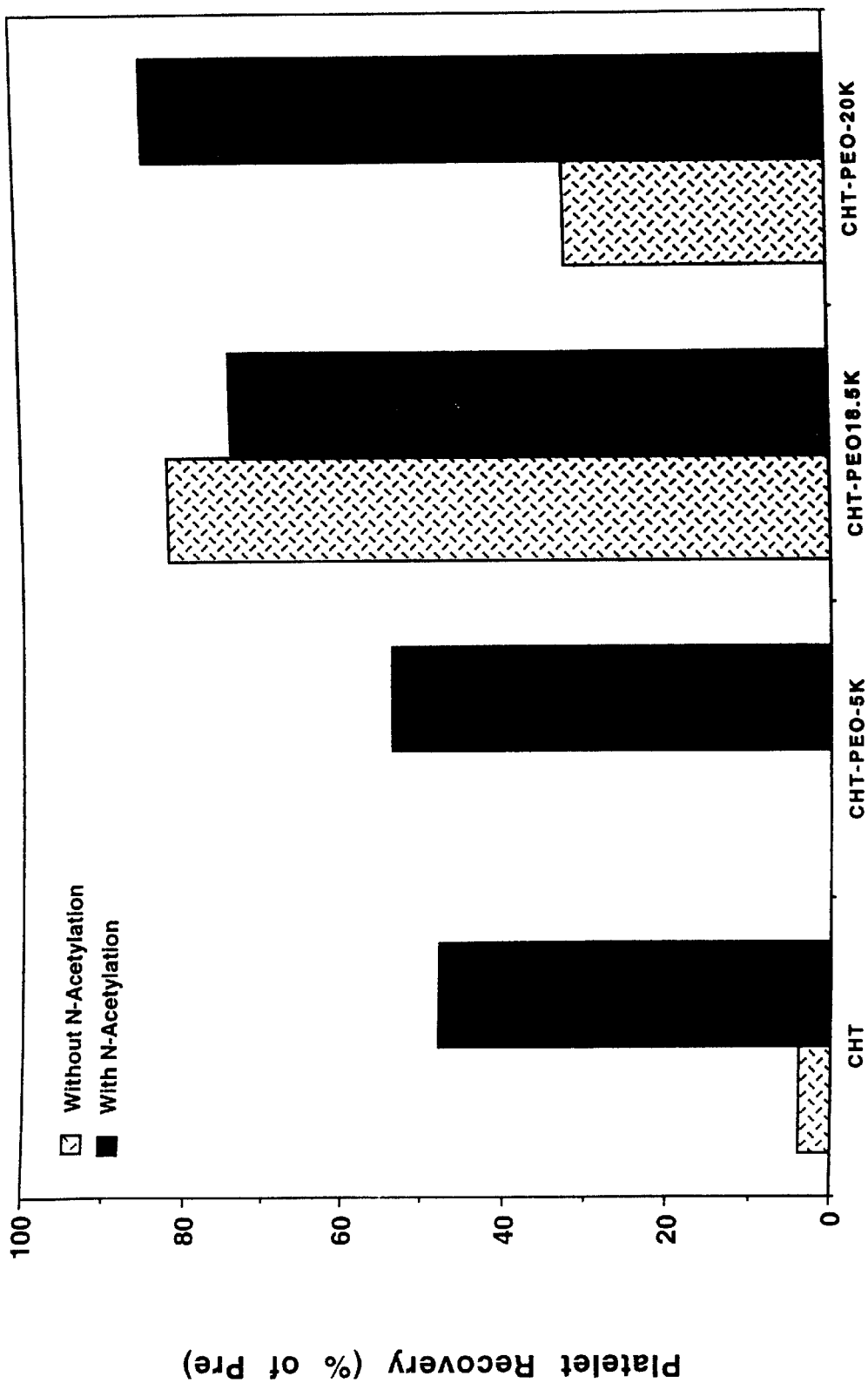
FIG. 12 illustrates graphically PEO coating on chitosan-treated glass filter mats with and without N-acetylation and the effect on platelet recovery from whole blood pursuant to Example 8.

3. Results:

PEO-coated chitosan mats showed an improved recovery of platelets and WBC, compared to chitosan-coated mats without additional PEO coating. N-acetylation of the free amine group of the chitosan molecules appears to improve WBC and platelet recovery even further compared to non-acetylated materials. Surfaces coated with HMW PEO appear to have performed better than surfaces coated with LMW PEO (see FIGS. 11 and 12).

B. PEO-Coated Heparin-Surfaces:

1. Attachment of PEO onto Heparin-fixed Denacol-treated Pericardial Heart Valve Tissues (HVT):

Two types of Heparin fixed Denacol treated tissues (3A and 4A) were obtained from Baxter CVG and were used for this study. They were washed several times with deionized water and were soaked in an oxycarbonyl imidazole-PEO (Imz-PEO) solution (pH=8.3) for 24 hours, followed by reaction with an amino-PEO ($NH_2$-PEO) at the same pH for at least 24 hours. Incubations were performed at room temperature.

2. Biocompatibility Evaluation:

PEO-coated and non-PEO-coated tissues were tested for their ability to bind fibrinogen (Fg) from a solution of purified human fibrinogen and from fresh whole blood according to the following procedure: PEO-coated and uncoated materials were soaked in a citrate phosphate buffer solution (pH=7.4) containing $^{125}$I-labeled fibrinogen (Fg), and were incubated at 37° C. for one hour. Unbound fibrinogen was removed from the materials by washing extensively with saline, then each sample was counted in a gamma counter. The amount of protein adsorbed was calculated from the specific activity of the fibrinogen and expressed as ng of protein per mg (or per surface area) of materials.

Figure 13:
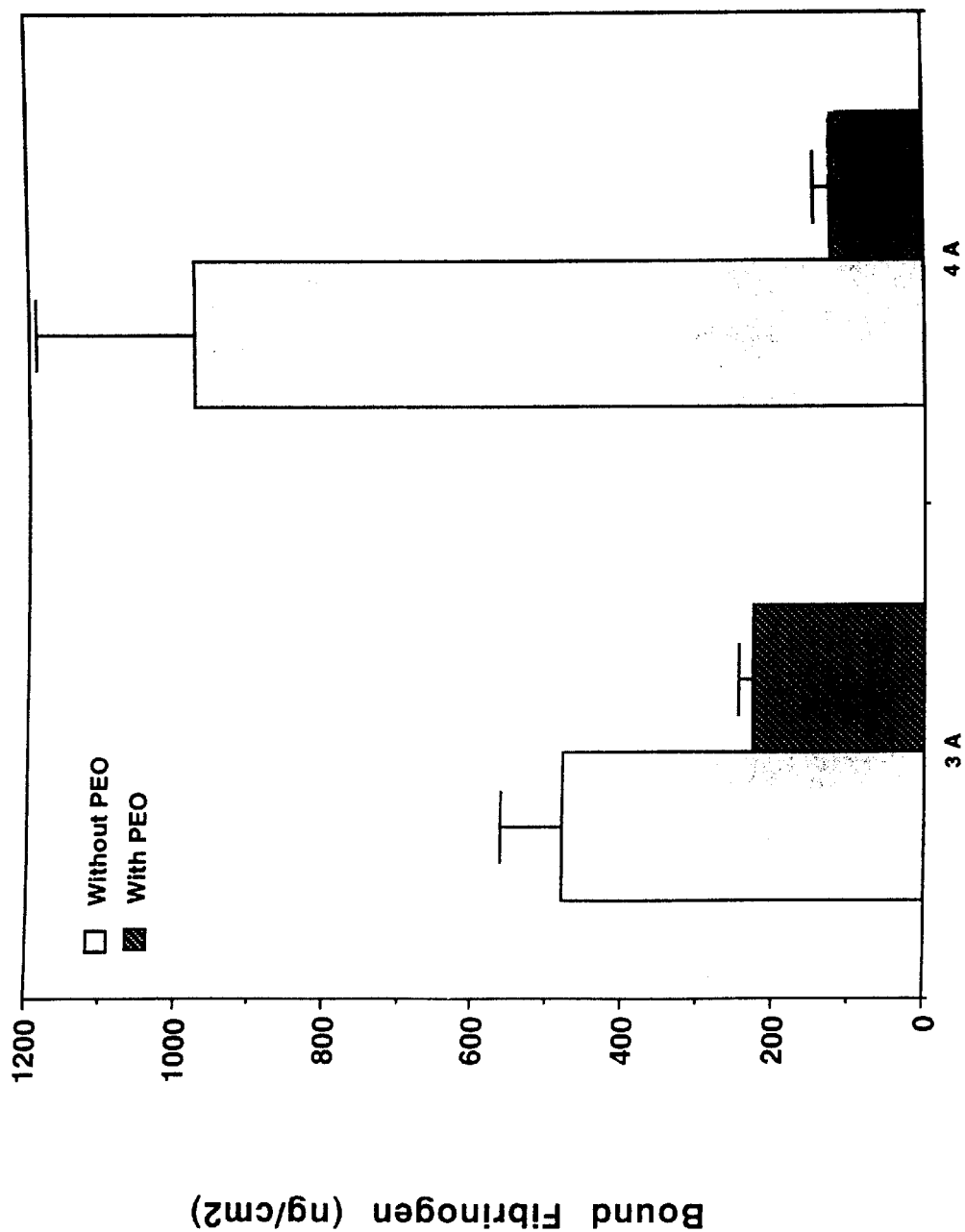
FIG. 13 illustrates graphically the effect of PEO coating on fibrinogen binding to heparinized-HVT (Tissues 4A were sterilized in solution containing glutaraldehyde, while tissues 3A were in sterile solution without glutaraldehyde).
Figure 14:
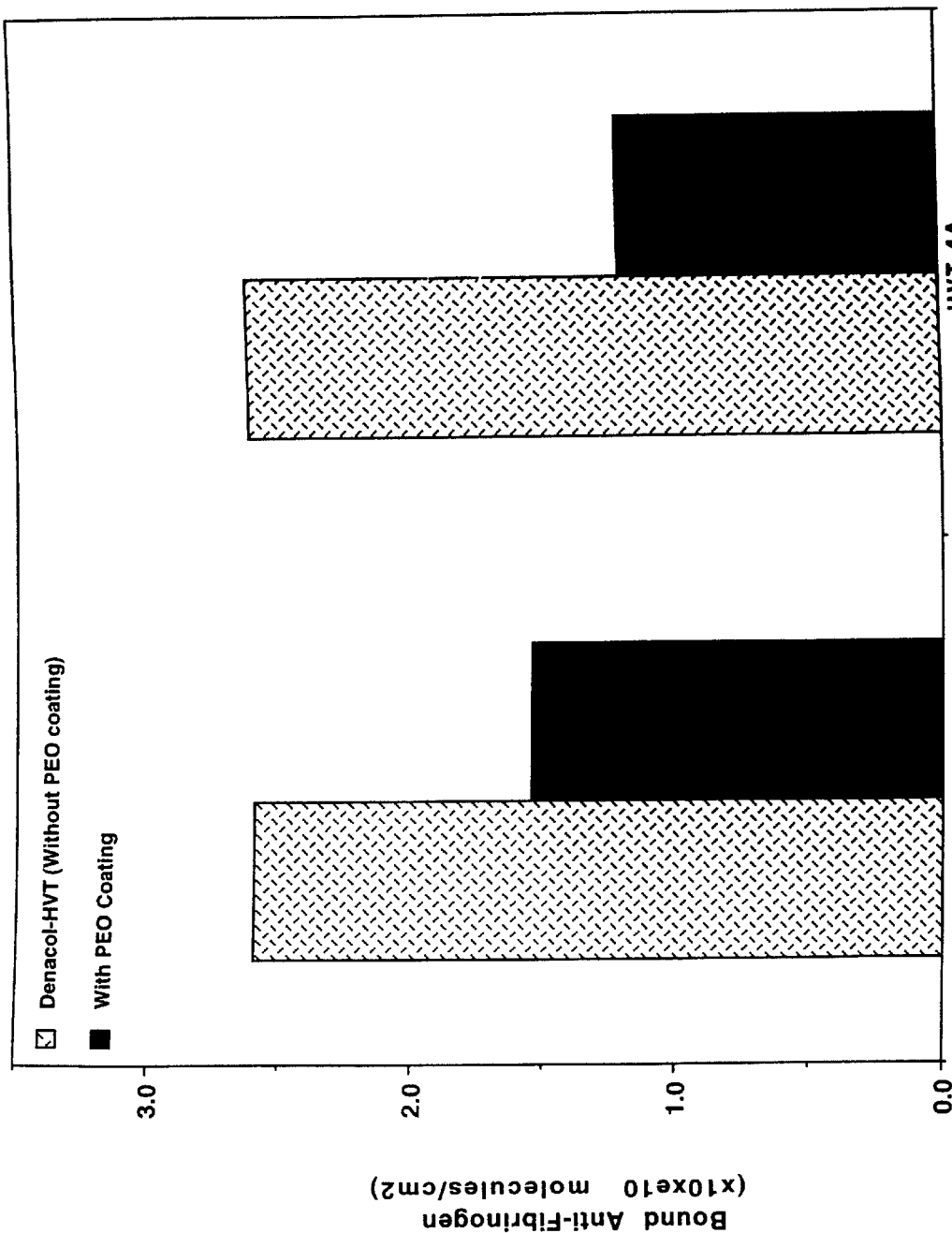
FIG. 14 illustrates graphically the effect of PEO coating on fibrinogen binding from whole blood exposured to Denacol treated bovine pericardial heart valve pursuant to Example No. 8.

3. Results:

The results indicate that PEO-coated heparinized HVT can significantly reduce fibrinogen binding from both sources, a purified solution of human Fg and Fg from whole blood, compared to uncoated tissues (see FIGS. 13 and 14).

C. Heparin-treated Imz-PEO-coated-HVT:

A Heparin coating procedure, similar to the one described in section 2a above, was applied in this study. Heparin solution (prepared in bicarbonate buffer pH=8.3) was used instead of amino-PEO to react with Imz-PEO-coated HVT.

It will be understood that various modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

We claim:

1. An implantable biological tissue having improved calcification mitigation properties, comprising:
   a biological tissue treated with one or more high molecular weight polyalkylene oxide derivatives.

2. The implantable biological tissue of claim 1, wherein the biological tissue is pre-treated with glutaraldehyde.

3. The implantable biological tissue of claim 2, wherein the pre-treatment includes cross-linking with glutaraldehyde.

4. The implantable biological tissue of claim 3, wherein the treatment with a high molecular weight polyalkylene oxide comprises treatment with an Imz-PEO solution.

5. The implantable biological tissue of claim 4, wherein the treatment with an Imz-PEO solution is followed by a reaction with $NH_2$-PEO.

6. The implantable biological tissue of claim 5, further including treating the tissue with a biologically active recognition sequence, peptide, or compound during the reaction with $NH_2$-PEO.

7. The implantable biological tissue of claim 6, wherein the treatment with an Imz-PEO solution is followed by a reaction with $NH_2$-PEO.

8. The implantable biological tissue of claim 1, wherein the biological tissue is selected from the group consisting of:
   bovine pericardial tissue;
   porcine tissue; and
   equine tissue.

9. The implantable biological tissue of claim 1, wherein the biological tissue is fresh and the treatment with a high molecular weight polyalkylene oxide comprises treatment with an Imz-PEO solution.

10. A method for improving the calcification mitigation properties of an implantable biological tissue, comprising the step of:
    treating a biological tissue with one or more high molecular weight polyalkylene oxide derivatives.

11. The method of claim 10, wherein the biological tissue is pre-treated with glutaraldehyde.

12. The method of claim 10, wherein the pre-treatment includes cross-linking with glutaraldehyde.

13. The method of claim 10, wherein the biological tissue is selected from the group consisting of:
    bovine pericardial tissue;
    porcine tissue; and
    equine tissue.

14. The method of claim 10, wherein the treatment with an Imz-PEO solution is followed by a reaction with $NH_2$-PEO.

15. The method of claim 14, further including treating the tissue with a biologically active recognition sequence, peptide, or compound during the reaction with $NH_2$-PEO.

16. The method of claim 10, wherein the biological tissue is fresh and the treatment with a high molecular weight polyalkylene oxide comprises treatment with an Imz-PEO solution.

17. The method of claim 16, wherein the treatment with an Imz-PEO solution is followed by a reaction with $NH_2$-PEO.

* * * * *